US011033873B2

(12) United States Patent
 Presley et al.

(10) Patent No.: US 11,033,873 B2
(45) Date of Patent: Jun. 15, 2021

(54) CONVERSION OF A HYDROGEN FLUORIDE ALKYLATION UNIT TO A SULFURIC ACID ALKYLATION UNIT AND APPARATUS UTILIZED THEREIN

(71) Applicant: Refining Technology Solutions, LLC, Overland Park, KS (US)

(72) Inventors: Christopher Shane Presley, Leawood, KS (US); Jason Brent Nunez, Lees Summit, MO (US); Diwakar Rana, Overland Park, KS (US); William Joseph Schwarzbach, Jr., Pearland, TX (US)

(73) Assignee: Refining Technology Solutions, LLC, Overland Park, KS (US)

( * ) Notice: Subject to any disclaimer, the term of this patent is extended or adjusted under 35 U.S.C. 154(b) by 0 days.

(21) Appl. No.: 16/641,823

(22) PCT Filed: Aug. 30, 2018

(86) PCT No.: PCT/US2018/048803
§ 371 (c)(1),
(2) Date: Feb. 25, 2020

(87) PCT Pub. No.: WO2019/046554
PCT Pub. Date: Mar. 7, 2019

(65) Prior Publication Data
US 2020/0197895 A1   Jun. 25, 2020

Related U.S. Application Data

(60) Provisional application No. 62/552,496, filed on Aug. 31, 2017.

(51) Int. Cl.
*B01J 14/00* (2006.01)
*B01J 19/24* (2006.01)
(Continued)

(52) U.S. Cl.
CPC .......... *B01J 14/00* (2013.01); *B01J 19/0013* (2013.01); *B01J 19/24* (2013.01); *C07C 2/62* (2013.01);
(Continued)

(58) Field of Classification Search
CPC ........ B01J 14/00; B01J 19/0013; B01J 19/24; B01J 2219/00024; B01J 2219/00006; C07C 2/62; C07C 2527/054
See application file for complete search history.

(56) References Cited

U.S. PATENT DOCUMENTS 2,511,758 A   6/1950   Weinrich
3,759,318 A   9/1973   Putney et al.
(Continued)

FOREIGN PATENT DOCUMENTS

WO        94/02437 A1    2/1994
WO    2011/006848 A1    1/2011

OTHER PUBLICATIONS

"Catalytic Alkylation", Petro/Chem Engineer, Dec. 1961 and Jan. 1962.
(Continued)

*Primary Examiner* — Lessanework Seifu

(57) ABSTRACT

This disclosure relates to methods of converting an HF alkylation unit which utilizes HF as a reaction catalyst to a sulfuric acid alkylation unit which utilizes sulfuric acid as a reaction catalyst. This disclosure also relates to a segmented sulfuric acid settler for separating a sulfuric acid phase from a hydrocarbon phase. This disclosure also relates to methods of converting a vertical HF acid settler to a segmented sulfuric acid settler. This disclosure also relates to converted sulfuric acid alkylation units and alkylation processes performed in the converted sulfuric acid alkylation units.

16 Claims, 19 Drawing Sheets

(51) Int. Cl.
 *C07C 2/62* (2006.01)
 *B01J 19/00* (2006.01)
(52) U.S. Cl.
 CPC ............... *B01J 2219/0011* (2013.01); *B01J 2219/00024* (2013.01); *C07C 2527/054* (2013.01)

(56) References Cited

U.S. PATENT DOCUMENTS

| | | |
|---|---|---|
| 4,018,846 A | 4/1977 | Mayer |
| 4,225,740 A | 9/1980 | Chapman et al. |
| 4,276,731 A | 7/1981 | Henggeler et al. |
| 4,371,731 A | 2/1983 | Washer |
| 4,383,977 A | 5/1983 | Hutson, Jr. et al. |
| 4,404,418 A | 9/1983 | Hutson, Jr. et al. |
| 4,423,277 A | 12/1983 | Stroud |
| 4,467,131 A | 8/1984 | Washer et al. |
| 4,513,165 A | 8/1985 | Van Pool |
| 4,777,323 A | 10/1988 | Hann et al. |
| 5,157,196 A | 10/1992 | Crossland et al. |
| 5,284,990 A | 2/1994 | Peterson et al. |
| 7,850,929 B2 | 12/2010 | Smith, Jr. et al. |
| 8,920,755 B2 | 12/2014 | Cleverdon et al. |
| 8,921,636 B2 | 12/2014 | Cleverdon et al. |
| 9,580,366 B2 | 2/2017 | Puett et al. |
| 2004/0222157 A1 | 11/2004 | Minhas et al. |
| 2012/0172646 A1 | 7/2012 | Liu et al. |

OTHER PUBLICATIONS

"Alkylation will be key process in reformulated gasoline era", Oil & Gas Journal, Nov. 12, 1990, pp. 79-92.
"H2SO4, HF processes compared, and new technologies revealed", Oil & Gas Journal, Nov. 26, 1990, pp. 70-77.
"Which alkylation—HF or H2SO4?", Hydrocarbon Processing, Sep. 1985.
International Search Report, PCT/US2018/048803, dated Oct. 23, 2018, 4 pages.
Written Opinion, PCT/US2018/048803, dated Oct. 23, 2018, 5 pages.
International Preliminary Report on Patentablity, PCT/US2018/048803, dated Mar. 3, 2020, 6 pages.
Cross, W. et al.,"Safer with Sulfur", Hydrocarbon Engineering (2010) 15, p. 59-66.

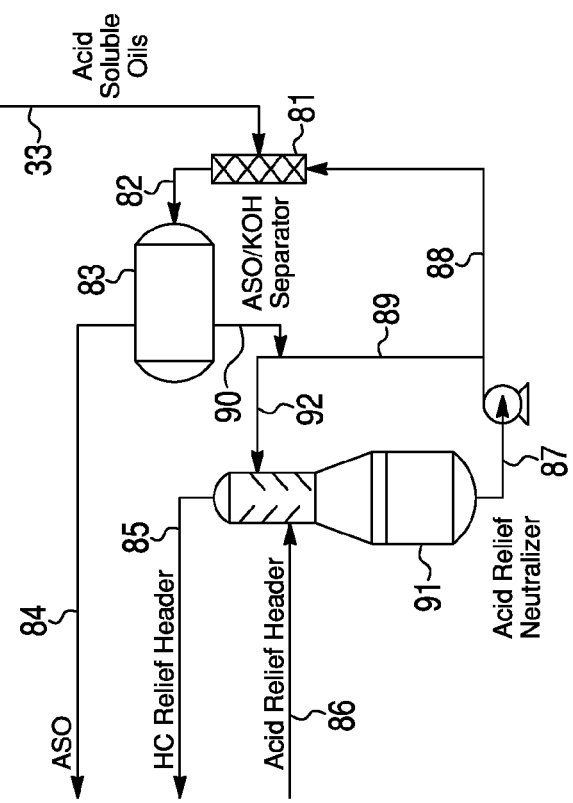
FIG. 1 (Prior Art) cont.

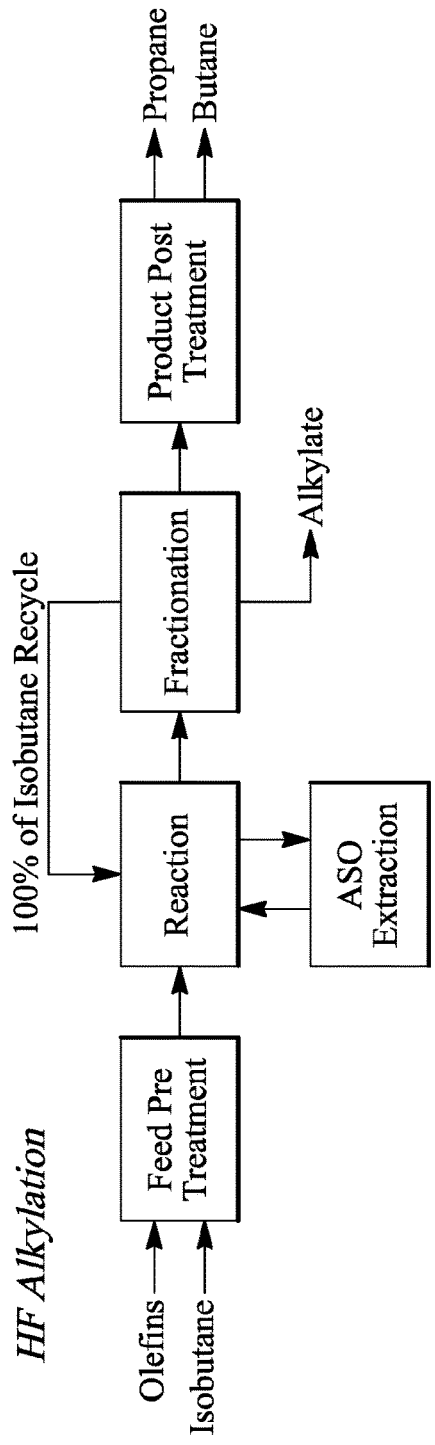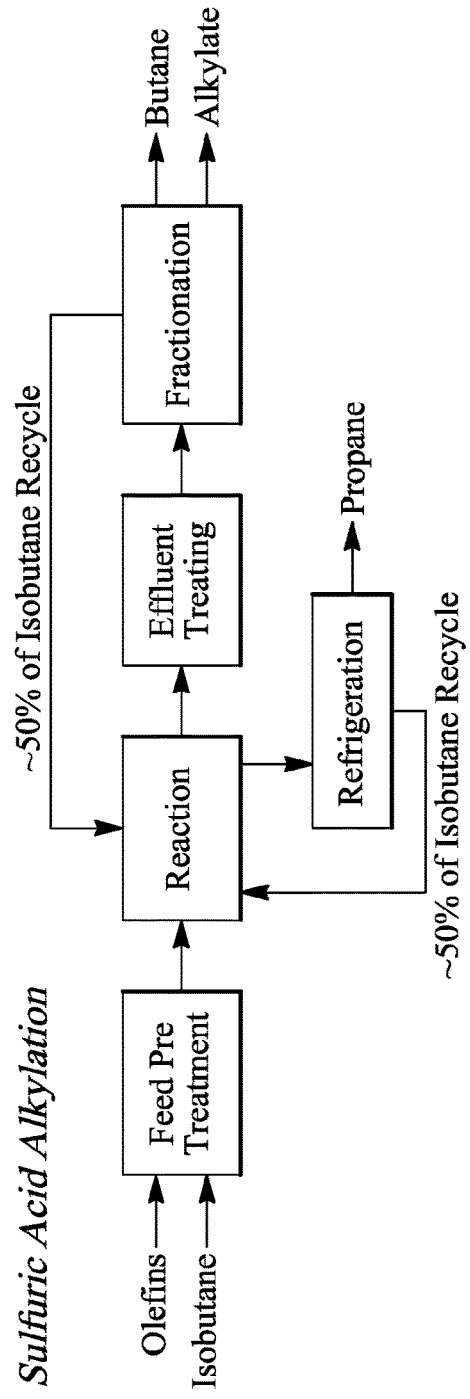

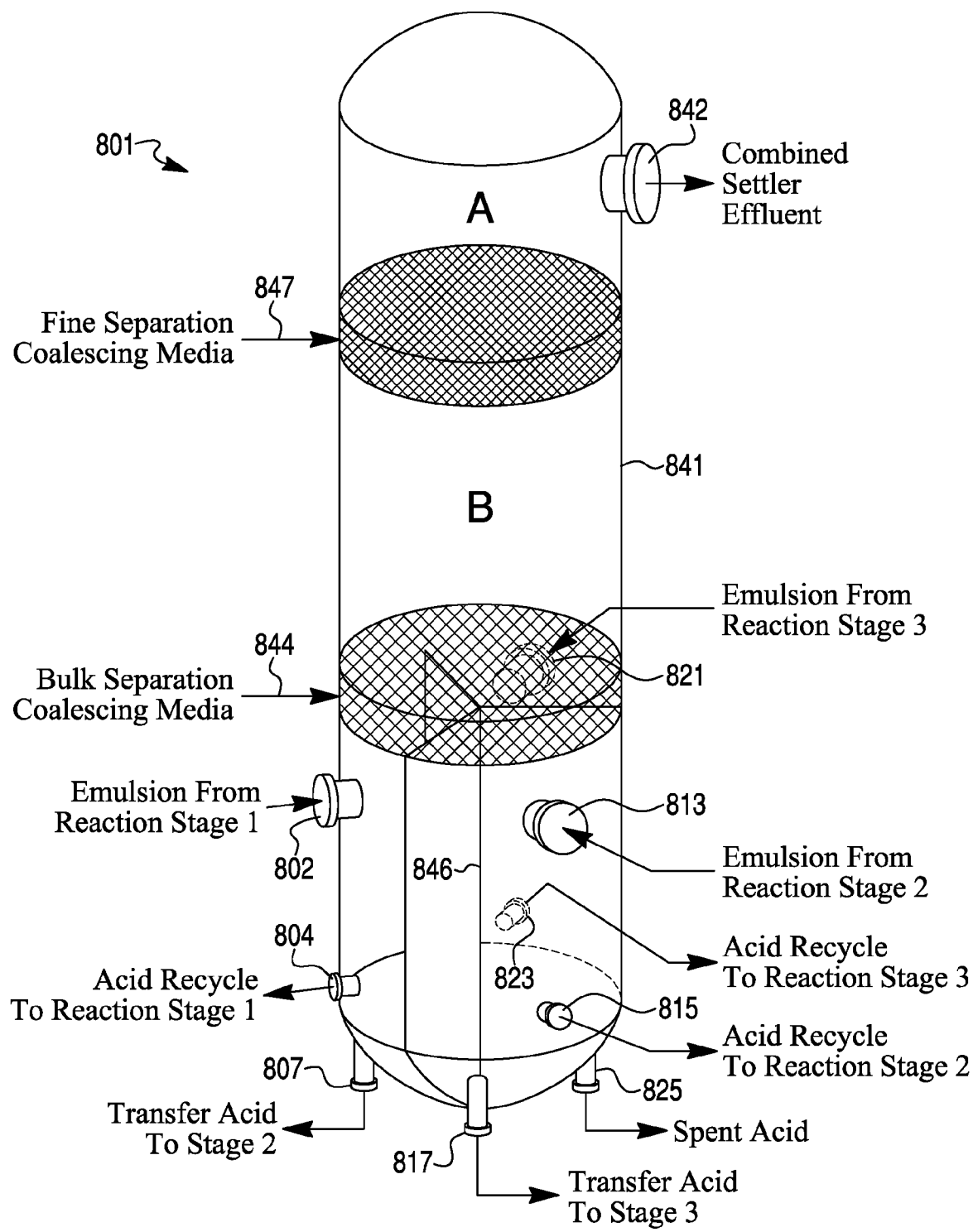

CONVERSION OF A HYDROGEN FLUORIDE ALKYLATION UNIT TO A SULFURIC ACID ALKYLATION UNIT AND APPARATUS UTILIZED THEREIN

CROSS-REFERENCE TO RELATED APPLICATION

This application claims priority of U.S. Patent Application 62/552,496 filed on Aug. 31, 2017, the disclosure of which is incorporated herein by reference in its entirety for all purposes.

BACKGROUND

Field of the Disclosure

The present disclosure relates to methods for conversion of a hydrogen fluoride (HF) catalyzed alkylation unit to a sulfuric acid (SA) catalyzed alkylation unit. The present disclosure also relates to apparatus and systems for use in SA catalyzed alkylation units which are newly added or retained from an existing HF catalyzed alkylation unit. The present disclosure also relates to a segmented sulfuric acid settler for separating a sulfuric acid phase from a hydrocarbon phase. The present disclosure also relates to converted SA alkylation units and alkylation processes performed therein.

Description of Related Art

Because of its clean-fuel properties (iso-paraffinic, high-octane, low-vapor pressure and very low sulfur), alkylate is considered one of the most desired components in the gasoline pool. As mandates for cleaner-burning fuel in the US and abroad have started to become fully realized, refiners are relying more than ever on alkylate to meet stringent gasoline specifications. With increasing pressure to reduce tailpipe emissions, the rapid decline of diesel in Europe and the modernization of automobiles worldwide, alkylate is well-positioned to be in steady demand for decades to come.

Most alkylate is produced in refineries by combining $C_3$-$C_5$ light olefins from the fluid catalytic cracker (FCC) with isobutane in a process called alkylation. The predominant alkylation technologies utilized by refiners require either sulfuric acid ($H_2SO_4$, SA) or hydrofluoric acid (HF) to catalyze the reaction. Although grassroots construction of sulfuric acid alkylation units has dominated the industry for the last 20 years, a very large number of HF alkylation units remain in operation. For example, in the US, approximately 100 alkylation units are in operation, with about half of them utilizing HF alkylation technology. Due to the volatile and toxic nature of HF, refiners have long sought out cost-effective solutions to convert HF alkylation units to safer sulfuric acid alkylation technology. However, with the perceived high cost of conversion and a lack of a regulatory requirement to make this change, refiners have yet to convert an HF alkylation unit to a sulfuric acid alkylation unit.

Whether involving an expansion of existing alkylation units, refinery grassroots alkylation units or stand-alone alkylation complexes utilizing feedstocks from nontraditional petrochemical sources, alkylation projects are of high interest in the energy sector. For refiners that operate HF alkylation units, the regulatory and community pressures to eliminate the use of HF have never been greater. This is especially a concern in those refineries operating near large metropolitan areas. Therefore, there is a need for cost-effective methods to convert existing HF catalyzed alkylation units to sulfuric acid (SA) catalyzed alkylation units.

BRIEF SUMMARY OF THE DISCLOSURE

The present disclosure provides a method for converting a hydrogen fluoride alkylation unit which utilizes hydrogen fluoride as a reaction catalyst to a sulfuric acid alkylation unit. The hydrogen fluoride alkylation unit comprises an HF alkylation reactor, an HF alkylation fractionation section comprising at least one fractionator, and an HF acid relief neutralizer vessel. The method comprises: (a) substituting sulfuric acid for hydrogen fluoride as the reaction catalyst; (b) retaining the HF acid relief neutralizer vessel as a blowdown vapor scrubber; (c) retaining the HF alkylation fractionation section as a sulfuric acid alkylation fractionation section; (d) providing at least one sulfuric acid alkylation reactor; (e) providing a refrigeration section comprising a refrigerant compressor and a heat exchanger for condensing a vapor stream from the refrigerant compressor; (f) providing a conduit for recycling an isoparaffin comprising isobutane from the refrigeration section to said at least one sulfuric acid alkylation reactor; and (g) providing a feed/effluent heat exchanger for cooling a hydrocarbon feed stream and heating a net effluent stream.

The present disclosure also provides a segmented sulfuric acid settler for separating a sulfuric acid phase from a hydrocarbon phase. The sulfuric acid settler comprises: (a) a vertical vessel having an outlet at its top section, a vertical interior wall, and a bottom; (b) at least one internal vertical wall defining two or more settling chambers within the vessel; (c) an inlet for each settling chamber for ingress of a sulfuric acid/hydrocarbon emulsion; (d) an outlet for each settling chamber located below the inlet for that settling chamber for exit of the sulfuric acid phase from that settling chamber; and (e) a coalescing media extending substantially the full diameter of the vertical vessel, the coalescing media being positioned above the at least one internal vertical wall.

The present disclosure also provides a method for converting a hydrogen fluoride alkylation unit which utilizes hydrogen fluoride as a reaction catalyst to a sulfuric acid alkylation unit. The method comprises: (a) substituting sulfuric acid for hydrogen fluoride as the reaction catalyst; and (b) modifying a suitable vessel in the hydrogen fluoride alkylation unit to provide a segmented sulfuric acid settler as disclosed in this disclosure.

The present disclosure also provides a method for converting a hydrogen fluoride alkylation unit which utilizes hydrogen fluoride as a reaction catalyst to a sulfuric acid alkylation unit. The method comprises: (a) substituting sulfuric acid for hydrogen fluoride as the reaction catalyst; and (b) providing a new segmented sulfuric acid settler as disclosed in this disclosure.

The present disclosure also provides a method for converting a vertical HF acid settler to a segmented sulfuric acid settler. The vertical HF acid settler comprises a vertical vessel having an outlet at its top section, a vertical interior wall, a bottom, and an internal baffle extending upwardly from the bottom of the vertical vessel. The method comprises: (a) retaining the internal baffle to provide at least one internal vertical wall defining settling chambers within the vessel, said internal vertical wall extending upwardly from the bottom of the vertical vessel; (b) retaining the outlet which is at the top section of the vertical vessel; (c) providing a first coalescing media extending substantially the full diameter of the vertical vessel, the first coalescing media being positioned above the internal vertical wall; and (d) providing an inlet and an outlet for each of said settling chambers, the outlet of a settling chamber being positioned below the inlet of said settling chamber.

The present disclosure also provides a method for converting a vertical HF acid settler to a segmented sulfuric acid settler. The vertical HF acid settler comprises a vertical vessel having an outlet at its top section, a vertical interior wall, a bottom, and internal components comprising an internal baffle extending upwardly from the bottom of the vertical vessel. The method comprises: (a) removing the internal components from the vertical vessel; (b) installing one or more internal vertical walls defining two or more settling chambers within the vessel, said one or more internal vertical walls extending upwardly from the bottom of the vertical vessel; (c) retaining the outlet which is at the top section of the vertical vessel; (d) providing a first coalescing media extending substantially the full diameter of the vertical vessel, the first coalescing media being positioned above the one or more internal vertical walls; and (e) providing an inlet and an outlet for each of said two or more settling chambers, the outlet of a settling chamber being positioned below the inlet of said settling chamber.

The present disclosure further provides converted sulfuric acid alkylation units as disclosed in this disclosure and alkylation processes performed in such converted sulfuric acid alkylation units.

Past literature on HF-to-SA alkylation conversion indicates an estimated cost of approximately 80% of a new grassroots sulfuric acid alkylation unit of the same size. The methods of this disclosure advantageously convert an existing HF alkylation unit to a SA alkylation unit at a significantly lower cost comparing with prior art disclosure through utilization of existing HF alkylation equipment. As a result, the costs of conversion methods provided in this disclosure are estimated at approximately 40%-60% of a new grassroots sulfuric acid alkylation unit, depending on the conversion method selected and the configuration of the existing HF alkylation unit. The conversion methods of this disclosure can also significantly increase capacity in the converted SA alkylation units at minimal additional cost.

BRIEF DESCRIPTION OF THE FIGURES

Embodiments are illustrated in the accompanying figures to improve understanding of concepts as presented herein.

FIG. 3 shows an overall process flow of a HF catalyzed alkylation unit.

FIG. 4 shows an overall process flow of a converted SA alkylation unit.

FIG. 5 is a schematic illustration of a segmented sulfuric acid settler of the present disclosure.

Figure 1:
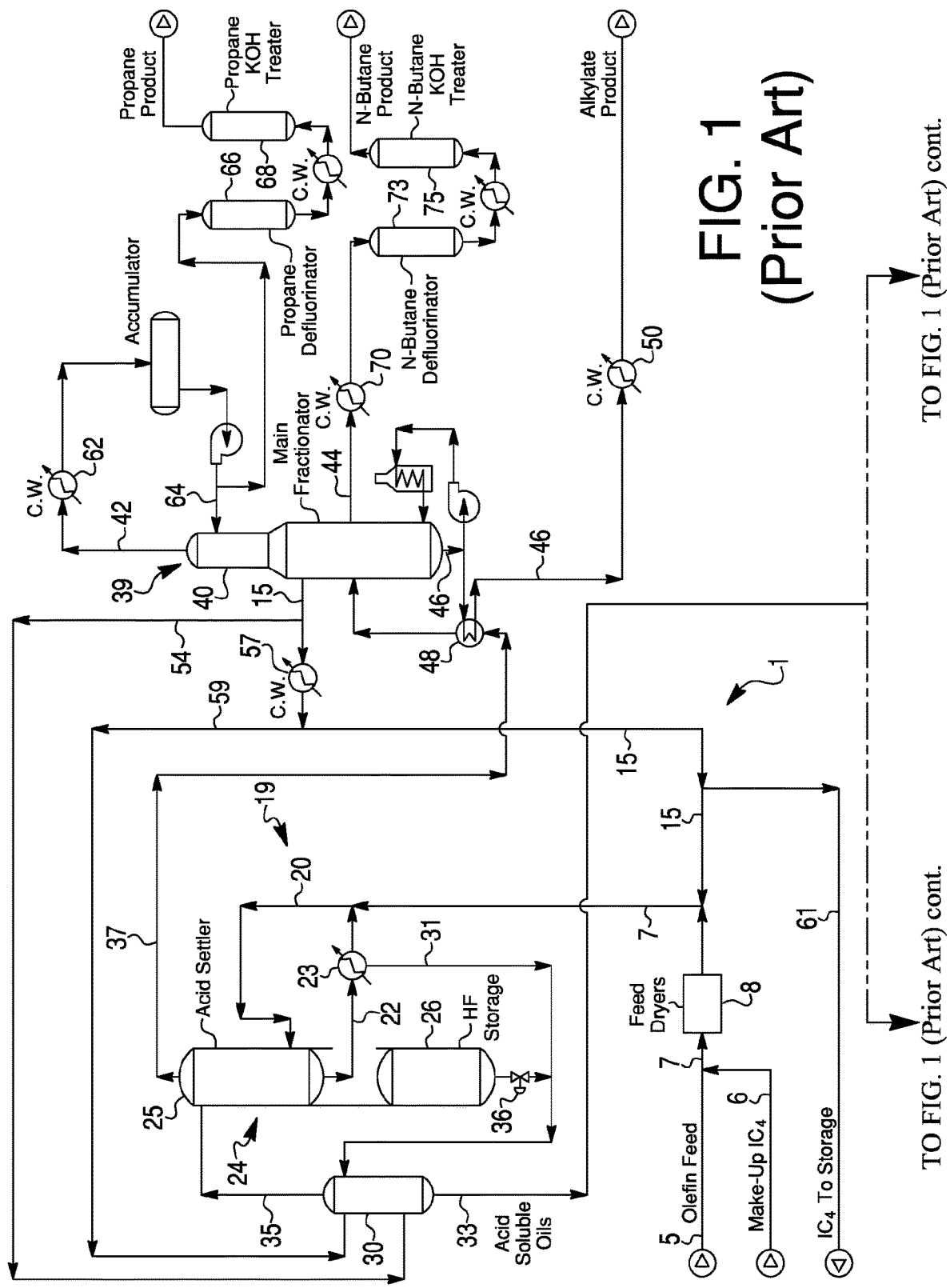
FIG. 1 is a schematic process flow diagram of a Phillips HF alkylation unit which uses HF as the reaction catalyst to produce alkylate.

Corresponding reference characters indicate corresponding parts throughout the drawings. Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments. Certain detailed features, such as pumps, heat exchangers or other ancillary equipment are not shown for the sake of simplicity and in order to demonstrate the main features of the alkylation unit or process.

DETAILED DESCRIPTION

The foregoing general description and the following detailed description are exemplary and explanatory only and are not restrictive of the invention, as defined in the appended claims. Specific process, structural and functional details disclosed herein are not to be interpreted as limiting, but merely as a basis for the claims and as a representative basis for teaching one skilled in the art to variously employ the present invention in virtually any appropriately detailed process and structure. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

Before addressing details of embodiments described below, some terms are defined or clarified.

The terms "retaining" or "retained", when used together with an equipment or a vessel in this disclosure, means the equipment or the vessel in an existing HF alkylation unit is kept, utilized or modified to become an equipment or a vessel in the converted SA alkylation unit. The equipment or the vessel from the existing HF alkylation unit can be used as it is or modified to fit in the converted SA alkylation unit. In some embodiments, the equipment or the vessel in the existing HF alkylation unit can be reused, modified or retrofitted to become the same kind of equipment or vessel in the converted SA alkylation unit. In some embodiments, the equipment or the vessel in the existing HF alkylation unit can be repurposed or modified to become a different kind of equipment or vessel in the converted SA alkylation unit.

The terms "decommissioning" or "decommissioned", when used together with an equipment or a vessel in this disclosure, means the equipment or the vessel in an existing HF alkylation unit is abandoned or no longer used in the converted SA alkylation unit during an alkylation process. The equipment or the vessel can remain in or be moved away from the site of the converted SA alkylation unit.

The term "new", when used together with an equipment or a vessel in this disclosure, means the equipment or the vessel added or provided to the converted SA alkylation unit is not previously present in the existing HF alkylation unit.

The term "converted SA alkylation unit(s)", as used herein, means a SA catalyzed alkylation unit provided by converting a HF catalyzed alkylation unit.

The term "remote HF storage tank", as used herein, means an HF storage tank located outside the battery limits of an HF alkylation unit.

The term "remote HF blowdown drum", as used herein, means an HF blowdown drum located outside the battery limits of an HF alkylation unit.

The term "olefin", as used herein, means an unsaturated hydrocarbon comprising one or more carbon-carbon double bonds. The unsaturated hydrocarbon herein does not include aromatic compounds. In some embodiments, the olefin has a single carbon-carbon double bond. In some embodiments, the olefin is a $C_3$ to $C_5$ olefin selected from the group consisting of propene, butenes, pentenes, and combinations thereof. In some embodiments, the olefin comprises propene. In some embodiments, the olefin comprises a butene selected from the group consisting of 1-butene, 2-butene, isobutene, and combinations thereof. 2-butene includes cis-2-butene and trans-2-butene. In some embodiments, the olefin comprises a pentene selected from the group consisting of 1-pentene and its branched isomers, 2-pentene and its branched isomers, and combinations thereof. 2-pentene includes cis-2-pentene and trans-2-pentene. In some embodiments, the olefin comprises a mixture of propene, butene and pentene.

The term "isoparaffin", as used herein, means isobutane, isopentane, or their mixtures. In some embodiments, the isoparaffin comprises, consists essentially of, or consists of an isobutane. In some embodiments, the isoparaffin comprises a mixture of isobutane and isopentane. In some embodiments, the isoparaffin is isobutane.

The term "net effluent", as used herein, means the liquid hydrocarbon phase of the alkylate product mixture generated at the end of the alkylation reaction in a converted SA alkylation unit. The net effluent typically comprises unreacted isoparaffin (e.g., isobutane), alkylate, and sulfur-containing contaminants such as residual sulfuric acid, alkyl sulfates, etc. In some embodiments, the net effluent further comprises propane and/or n-butane. In some embodiments, the net effluent is sent to a refrigeration section to remove low boiling components (e.g., propane and a portion of isobutane) before being sent to the feed/effluent heat exchanger. The net effluent can be purified and fractionated to produce an alkylate product.

The term "sulfuric acid alkylation reaction zones (stages) disposed in sequence", as used herein, means that the spent acid solution from at least one non-final reaction zone (stage) is sent to the immediately subsequent reaction zone (stage) as part or all of the sulfuric acid solution therein, that is, spent acid solution from a non-final reaction zone (stage) can be reused as catalyst in the immediately subsequent reaction zone (stage). A portion of the spent acid solution from the final reaction zone (stage) can be recycled to the final reaction zone (stage), and the rest is purged, that is, the spent acid solution from the final reaction zone (stage) is not reused in another reaction zone (stage). In some embodiments, the spent acid solution from each non-final reaction zone (stage) is sent to the immediately subsequent reaction zone (stage) as part or all of the sulfuric acid solution therein. Fresh sulfuric acid is fed into the first reaction zone (stage). In some embodiments, fresh sulfuric acid can also be fed into other non-final reaction zones (stages). Fresh sulfuric acid is typically not fed into the final reaction zone (stage). In some embodiments, the reaction zone (stage) is a sulfuric acid alkylation reactor. In some embodiments, the reaction zone (stage) is an internally agitated sulfuric acid alkylation reactor. In some embodiments, a reaction zone (stage) can comprise two or more reactors.

The term "spent acid solution", as used herein, refers to the sulfuric acid solution exiting a reaction zone (stage) at the end of the alkylation reaction. Typically, a spent acid solution comprises sulfuric acid, water, acid soluble oils, and reaction intermediates such as sulfate esters. The spent acid solution exits a reaction zone (stage) in the form of a sulfuric acid/hydrocarbon emulsion. Typically, the sulfuric acid/hydrocarbon emulsion is introduced into a sulfuric acid settler wherein a hydrocarbon phase is allowed to separate from a sulfuric acid phase of the sulfuric acid/hydrocarbon emulsion. A portion of the sulfuric acid phase comprising, consisting essentially of, or consisting of the spent acid solution from a reaction zone (stage) can be recycled to the same reaction zone (stage). Another portion or the non-recycled portion of the sulfuric acid phase comprising, consisting essentially of, or consisting of the spent acid solution from the reaction zone (stage) can be directed to or introduced into the immediately subsequent reaction zone (stage) as part or all of the sulfuric acid solution therein.

The term "fresh sulfuric acid", as used herein, means a sulfuric acid solution which has not been used as the catalyst in an alkylation reaction. The fresh sulfuric acid solution is essentially free of acid soluble oils and alkylation intermediates such as sulfate esters. In some embodiments, the acid strength of the fresh sulfuric acid is in the range of from about 96.5 wt % to about 99.5 wt %.

The term "alkylate", as used herein, means the reaction products generated in alkylation reactions between an olefin and an isoparaffin in the presence of a sulfuric acid catalyst or an HF catalyst. Alkylates typically are highly branched paraffinic hydrocarbons. Refiners use alkylate as a gasoline blend stock to boost octane, reduce Reid vapor pressure ("RVP"), and reduce olefin content in the final gasoline blend.

The term "acid strength", as used herein, means the concentration of the sulfuric acid solution which is expressed in weight percent $H_2SO_4$ as determined by titration with standardized sodium hydroxide. Diluents that can reduce the acid strength of a sulfuric acid solution include water, acid soluble oils formed by side reactions during an alkylation process, and reaction intermediates such as sulfate esters formed during an alkylation reaction.

The term "capacity", when used in connection with an alkylation unit, means the amount of alkylate the alkylation unit can produce per day.

The term "wt %", as used herein, means percentage by weight.

The term "wppm", as used herein, means parts per million by weight.

Alkylation processes in general are well known to those of skill in the art. For example, see "Catalytic Alkylation", Petri/Chem Engineer, December 1961 and January 1962, "Alkylation will be key process in reformulated gasoline era", Oil & Gas Journal, Nov. 12, 1990, pp. 79-92, "$H_2SO_4$, HF processes compared, and new technologies revealed", Oil & Gas Journal, Nov. 26, 1990, pp. 70-77, and "Which alkylation—HF or $H_2SO_4$?", Hydrocarbon Processing, September 1985, all herein incorporated by reference in its entirety for all purposes. Additionally, alkylation is generally disclosed in U.S. Pat. Nos. 4,018,846; 4,225,740; 4,276,731; 4,371,731; 4,383, 977; 4,404,418; 4,467,131; 4,513,165; 4,777,323; and 5,157,196; all herein also incorporated by reference in its entirety for all purposes.

U.S. Pat. No. 5,284,990 to Peterson et al. disclosed a method for converting an HF alkylation unit to a SA alkylation unit, the disclosure of which is incorporated herein by reference in its entirety for all purposes.

The present disclosure provides a method for converting a hydrogen fluoride (HF) alkylation unit which utilizes HF as a reaction catalyst to a sulfuric acid (SA) alkylation unit which utilizes SA as a reaction catalyst. One example of the HF alkylation unit is depicted in FIG. 1 which is a simplified process flow diagram of an HF alkylation unit 1 designed by Phillips Petroleum Company ("Phillips HF alkylation unit" or "gravity-flow HF alkylation unit"). Light olefins (olefins having three to five carbon atoms such as propylene, butylenes and amylenes) in an olefin feed stream 5 and isobutane in a make-up isobutane feed stream 6 are mixed in a hydrocarbon feed stream 7. The hydrocarbon feed stream 7 then passes through feed dryers 8 to dry the light olefins and isobutane. Propane and n-butane are present in the olefin feed stream 5 but do not react with isobutane. The propane and n-butane act merely as diluents for the reaction. Additional isobutane is added to the hydrocarbon feed stream from a recycle isobutane stream 15.

The hydrocarbon feed stream 7 is directed to a reaction section 19 comprising a HF alkylation reactor 20. The HF alkylation reactor generally comprises a pipe which is typically about fifty feet long and sized for the unit's capacity. The reactor may also be referred to as a reactor pipe or a reactor riser. In the reactor 20 the light olefins and isobutane combine or mix with HF from an HF recycle stream 22. Some mechanical mixing is generally provided to ensure thorough dispersion or mixing of isobutane and light olefins with the HF to promote alkylation.

To provide the necessary mechanical mixing to uniformly disperse isobutane and light olefins in the HF, the dried mixture of isobutane and light olefins is introduced into the HF alkylation reactor 20 through nozzles (not shown) at fairly high velocities. The injection of the light olefins and isobutane into the reactor 20 at fairly high velocities results in the formation of an HF reaction emulsion comprising isobutane and light olefins thoroughly distributed throughout the HF. With HF acting as a catalyst, the light olefins react with the isobutane in the HF reaction emulsion to produce alkylate.

Because the optimum reaction rate for HF catalyzed alkylation occurs at temperatures on the order of 80° Fahrenheit (F) to 110° F., the HF in the HF recycle stream 22 is cooled prior to mixing with the light olefins and isobutane in the dry hydrocarbon feed stream 7. Cooling of the HF recycle stream 22 occurs in cooling means such as an HF acid cooler 23 which comprises a shell and tube heat exchanger. HF is passed through the shell side of the exchanger and cooling water is passed through the tube side of the exchanger to reduce the temperature of the HF to approximately 80° to 110° F.

The HF reaction emulsion rises in the reactor 20 which is uncooled and enters a settling section 24 comprising a vertical HF acid settler 25 wherein a hydrocarbon phase is allowed to separate from an HF acid phase of the HF reaction emulsion. The settling time necessary to allow separation of the HF acid phase from the hydrocarbon phase is relatively short, on the order of five minutes. The resulting hydrocarbon phase comprises mainly isobutane and alkylate with some propane, n-butane, dissolved HF and isoalkyl fluorides. The HF acid phase comprises primarily HF with some acid-soluble oils and water dissolved therein. The vertical HF acid settler 25 is in a top section of a large two-section vertical column. Fresh liquid HF is stored in a bottom section or HF storage tank 26 under the vertical HF acid settler of the two-section vertical column.

HF in the HF acid phase continuously leaves the bottom of the vertical HF acid settler 25 because of gravity and enters the HF recycle stream 22. As discussed above the HF recycle stream 22 is directed through the HF acid cooler 23 to remove the heat of reaction from the HF recycle stream 22 and reduce the temperature of the HF recycle stream 22 to approximately 80° to 110° F.

A portion of the HF acid phase is separated from the HF recycle stream 22 out of the HF acid cooler 23 and directed to an HF regenerator 30 through HF slipstream 31. Acid soluble oils present in the HF acid phase are stripped therefrom in the HF regenerator using isobutane as a stripper. The acid soluble oils are removed from the bottom of the HF regenerator 30 in an acid soluble oil (ASO) stream 33. HF and isobutane are directed from the HF regenerator 30 back to the vertical HF acid settler 25 through HF acid return stream 35. Fresh HF may be introduced into the vertical HF acid settler 25 by opening valve 36 to the HF storage tank 26 under the vertical HF acid settler to allow HF to flow through HF slipstream 31, HF regenerator 30 and HF acid return stream 35 to the vertical HF acid settler 25.

The hydrocarbon phase is drawn from the vertical HF acid settler 25 through a hydrocarbon effluent stream 37 and is fed to an HF alkylation fractionation section 39 comprising a main fractionator 40. The main fractionator separates the hydrocarbon phase into four streams: an overhead or top stream 42 which comprises a mixture of HF and propane; the recycle isobutane stream 15 which is mainly isobutane and which is recycled to the HF alkylation reactor 20 with the dry hydrocarbon feed stream 7; a vapor side stream 44 which comprises mainly n-butane; and a bottom stream 46 which comprises primarily alkylate. The hydrocarbon effluent stream 37 is heated prior to entry into the main fractionator 40 by passing the hydrocarbon phase in the hydrocarbon effluent stream 37 through the shell side of a feed/bottoms heat exchanger 48 and passing the bottom stream 46 through the tube side of the feed/bottoms heat exchanger 48. The alkylate in the bottom stream 46 is further cooled using an alkylate product cooler 50 which uses cooling water as a coolant.

A first portion of isobutane in the recycle isobutane stream 15 is diverted to the HF regenerator 30 through isobutane stripping stream 54. The isobutane in the isobutane stripping stream 54 is used to strip HF from a mixture of HF and acid soluble oils in the HF regenerator 30. After the first portion of isobutane is removed from the recycle isobutane stream 15, the recycle isobutane stream 15 passes through a recycle isobutane cooler 57 which uses cooling water as a coolant to cool the recycle isobutane stream 15. After the isobutane in the recycle isobutane stream 15 is cooled in the recycle isobutane cooler 57, a second portion of isobutane is separated from the recycle isobutane stream 15 and directed to the HF regenerator 30 through isobutane reflux stream 59 to facilitate stripping of acid soluble oils from the mixture of HF and acid soluble oils. A third portion of isobutane is separated from the recycle isobutane stream 15 and directed to storage through isobutane storage stream 61 which is optional.

A propane HF stripper (not shown) is provided to separate HF from propane in the top stream 42. The top stream 42 is cooled in a propane condenser 62. A portion of the top stream 42 comprising primarily propane is directed back into the main fractionator 40 through propane reflux stream 64. The remainder of top stream 42 is directed through a propane defluorinator 66 and a propane KOH (potassium hydroxide) treater 68 to remove isoalkyl fluorides and hydrogen fluoride respectively.

The n-butane rich vapor side stream 44 is passed through a butane condenser 70 and then an n-butane defluorinator 73 to remove isoalkyl fluorides and an n-butane KOH treater 75 to remove hydrogen fluoride. In some embodiments, the propane defluorinator and/or the n-butane defluorinator uses alumina in the vessel as the defluorinating agent to remove isoalkyl fluorides. In some embodiments, the propane KOH treater and/or the n-butane KOH treater contains solid KOH in the vessel to neutralize HF.

The acid soluble oil stream 33 is directed to a static mixer 81 wherein the acid soluble oil (ASO) is mixed with an aqueous KOH solution 88, and the acidic components contained in the ASO are neutralized. The ASO/KOH mixture 82 is introduced into a ASO/KOH separator 83 wherein ASO 84 is allowed to separate from the aqueous KOH solution 90 which is directed to an HF acid relief neutralizer 91. The HF acid relief neutralizer 91 in an HF alkylation unit is used to neutralize vapor streams and carryover liquids (if present) that may be received from an HF acid relief (flare) header 86 during an upset when equipment in the HF alkylation unit needs to be rapidly depressurized. After the vapor streams and carryover liquids (if present) are neutralized by the aqueous KOH solution in the HF acid relief neutralizer 91, a hydrocarbon stream 85 comprising hydrocarbons contained in the vapor streams and carryover liquids (if present) exits the HF acid relief neutralizer 91 and is directed to a hydrocarbon (HC) relief (flare) header. The aqueous KOH solution 87 can be recycled. A first portion of the recycle KOH solution 88 is directed to the static mixer 81. A second portion of the recycle KOH solution 89 is combined with the aqueous KOH solution 90 from the ASO/KOH separator 83 to form a combined aqueous KOH solution stream 92 which is introduced into the HF acid relief neutralizer 91.

Figure 2:
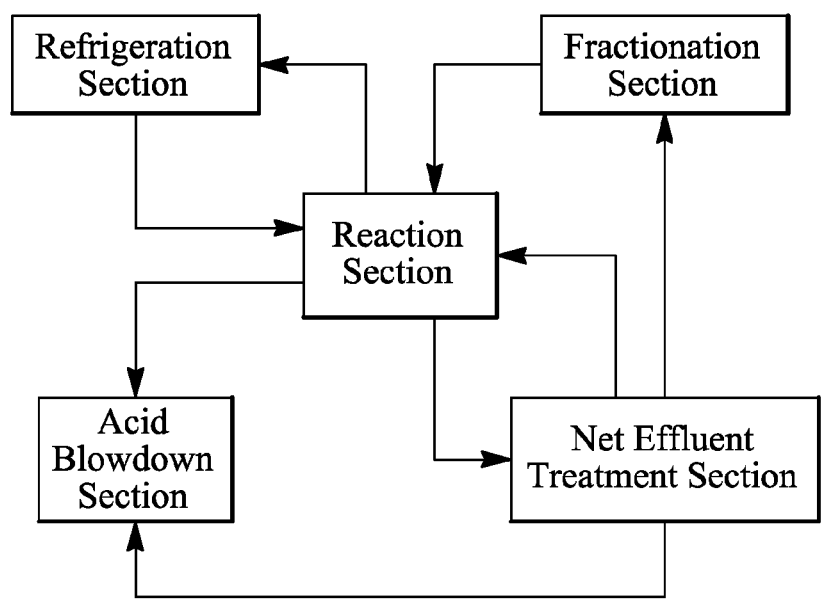
FIG. 2 is a block-flow diagram showing sections of grassroots and/or converted SA alkylation units.

In some embodiments, a converted SA alkylation unit comprises a reaction section, a refrigeration section, a fractionation section, a net effluent treatment section and an acid blowdown section as shown in FIG. 2. The reaction section typically comprises an alkylation reaction zone (stage) and a sulfuric acid settler. The refrigeration section helps to keep the reaction temperature low in the reaction section by sending a refrigerant recycle stream comprising isoparaffin reactant back to the reaction section. The fractionation section generates alkylate product and recovers and recycles unreacted isoparaffin reactant to the reaction section. The net effluent treatment section purifies the net effluent stream. The acid blowdown section is used to remove and/or recover residual hydrocarbons from the spent acid before sending the spent acid to storage.

Figure 7:
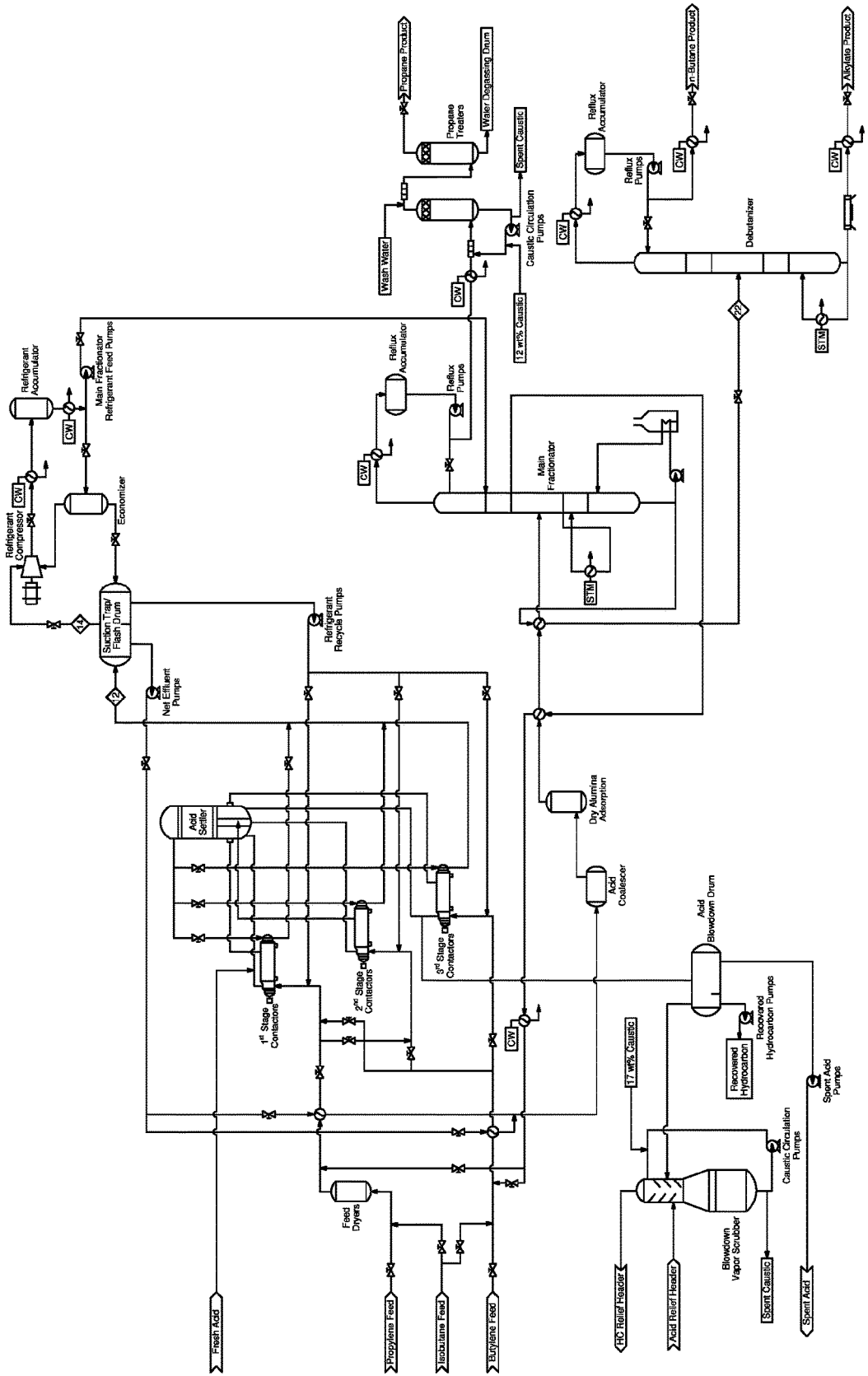
FIG. 7 is an overall schematic process flow diagram of a converted SA alkylation unit.
Figure 8:
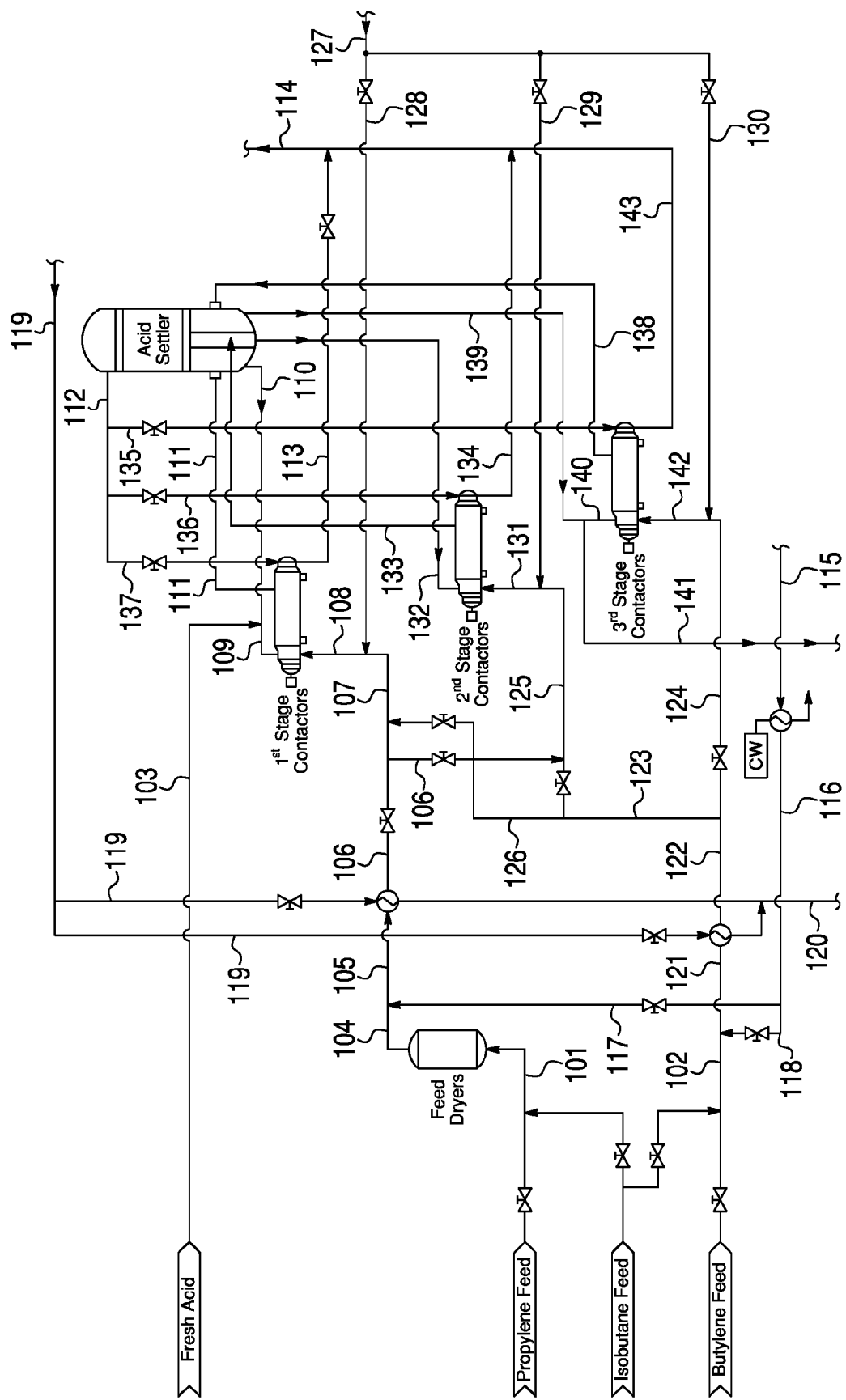
FIG. 8 is a schematic process flow diagram of the reaction section of the converted SA alkylation unit of FIG. 7.

FIGS. 7 to 14 depict an example of a converted SA alkylation unit which is converted from a Phillips HF alkylation unit (gravity-flow HF alkylation unit). FIG. 8 is a schematic process flow diagram of the reaction section of the converted SA alkylation unit of FIG. 7. FIG. 8 shows a segmented sulfuric acid settler (Acid Settler in FIG. 8) having three settling chambers within the vessel and three sulfuric acid alkylation reactors ($1^{st}$ Stage Contactors, $2^{nd}$ Stage Contactors, and $3^{rd}$ Stage Contactors) connected or coupled with the three settling chambers respectively to form one-to-one correspondence. The segmented sulfuric acid settler is provided by modifying the vertical HF acid settler (Acid Settler 25 as shown in FIG. 1). The sulfuric acid alkylation reactors in FIGS. 7 and 8 are DuPont STRATCO® Contactor™ reactors which are generally disclosed in U.S. Pat. Nos. 3,759,318 and 9,580,366, both are herein incorporated by reference in their entirety for all purposes.

FIG. 8 is a schematic process flow diagram of the reaction section of the converted SA alkylation unit of FIG. 7. A propylene feed is mixed with an isobutane feed to form a propylene/isobutane feed mixture 101 which passes through feed dryers to dry the feed mixture. The feed dryers 8 as shown in FIG. 1 in the HF alkylation unit are retained as the feed dryers in this converted SA alkylation unit. A recycle isobutane stream 115 is cooled by a cold water heat exchanger to form a cooled recycle isobutane stream 116. A portion of the cooled recycle isobutane stream is added to the dried propylene/isobutane feed mixture 104 to form a first hydrocarbon feed stream 105. The first hydrocarbon feed stream 105 is cooled prior to entry into a sulfuric acid alkylation reactor by passing through a first feed/effluent heat exchanger to transfer heat to a net effluent 119.

Figure 13:
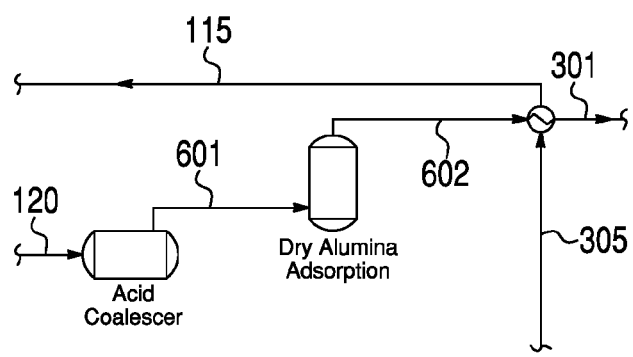
FIG. 13 is a schematic process flow diagram of the net effluent treatment section of the converted SA alkylation unit of FIG. 7.

A butylene feed is mixed with an isobutane feed to form a butylene/isobutane feed mixture 102 which is added with another portion of the cooled recycle isobutane stream 118 to form a second hydrocarbon feed stream 121. The second hydrocarbon feed stream 121 is cooled prior to entry into a sulfuric acid alkylation reactor by passing through a second feed/effluent heat exchanger to transfer heat to a net effluent 119. The heated net effluent 120 is directed to the net effluent treatment section as shown in FIG. 13.

A refrigerant recycle stream 127 comprising additional isobutane from the refrigeration section (FIG. 9) is split into three streams 128, 129 and 130. A portion of the cooled first hydrocarbon feed stream 106 is mixed with a portion of the cooled second hydrocarbon feed stream 126 and a portion of a refrigerant recycle stream 128 to form a hydrocarbon feed 108 to a first sulfuric acid alkylation reactor ($1^{st}$ Stage Contactors). A portion of the cooled first hydrocarbon feed stream 106 is mixed with a portion of the cooled second hydrocarbon feed stream 125 and a portion of a refrigerant recycle stream 129 to form a hydrocarbon feed 131 to a second sulfuric acid alkylation reactor ($2^{nd}$ Stage Contactors). A portion of the cooled second hydrocarbon feed stream 124 is mixed with a portion of a refrigerant recycle stream 130 to form a hydrocarbon feed 142 to a third sulfuric acid alkylation reactor ($3^{rd}$ Stage Contactors).

A fresh sulfuric acid stream 103 is added to a sulfuric acid recycle stream 110 from the outlet of a first settling chamber to form a sulfuric acid feed 109 to the first sulfuric acid alkylation reactor. A sulfuric acid/hydrocarbon emulsion 111 exiting the first sulfuric acid alkylation reactor is directed to an inlet of the first settling chamber of the segmented sulfuric acid settler. In the segmented sulfuric acid settler, a hydrocarbon phase is allowed to separate from a sulfuric acid phase of the sulfuric acid/hydrocarbon emulsion. The sulfuric acid phase exiting an outlet of the first settling chamber is recycled to the first sulfuric acid alkylation reactor as the sulfuric acid recycle stream 110. In some embodiments, a portion of the sulfuric acid phase exiting the outlet of the first settling chamber is directed to the second sulfuric acid alkylation reactor. The hydrocarbon phase from the first settling chamber rises above the settling chambers to be combined with hydrocarbon phases from the second and third settling chambers. The combined hydrocarbon phase exits the segmented sulfuric acid settler from an outlet at its top section to form a hydrocarbon effluent stream 112.

Similarly, a sulfuric acid/hydrocarbon emulsion 133 exiting the second sulfuric acid alkylation reactor is directed to an inlet of the second settling chamber of the segmented sulfuric acid settler. In the segmented sulfuric acid settler, a hydrocarbon phase is allowed to separate from a sulfuric acid phase of the sulfuric acid/hydrocarbon emulsion. The sulfuric acid phase exiting an outlet of the second settling chamber is recycled to the second sulfuric acid alkylation reactor as the sulfuric acid recycle stream 132. In some embodiments, a portion of the sulfuric acid phase exiting the outlet of the second settling chamber is directed to the third sulfuric acid alkylation reactor. The hydrocarbon phase from the second settling chamber rises above the settling chambers to be combined with hydrocarbon phases from the first and third settling chambers to form the hydrocarbon effluent stream 112.

Figure 14:
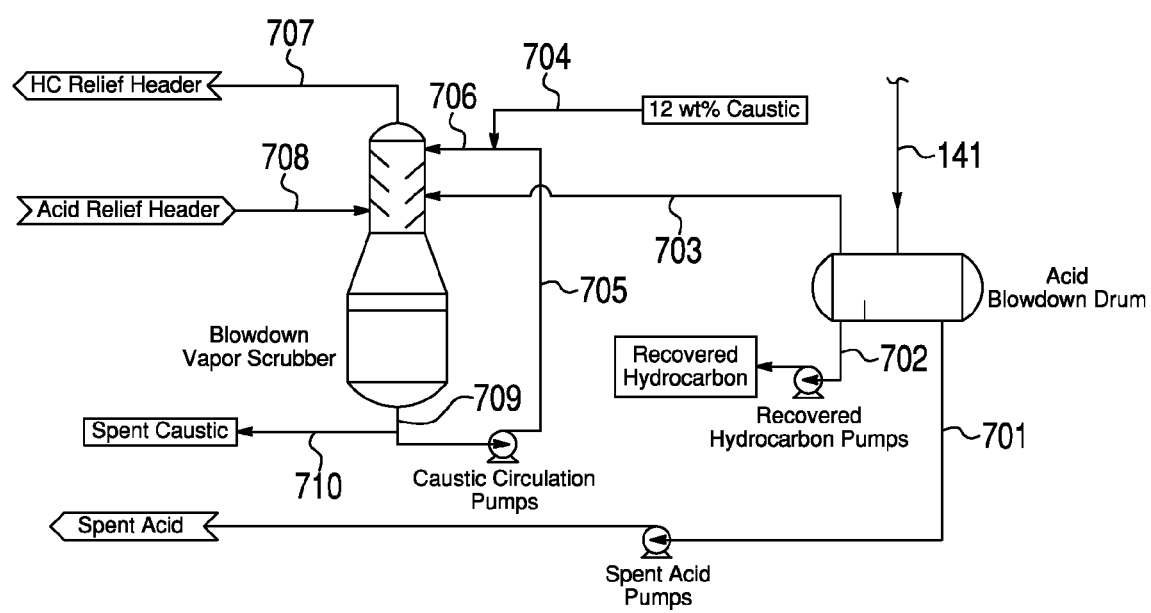
FIG. 14 is a schematic process flow diagram of the sulfuric acid blowdown section of the converted SA alkylation unit of FIG. 7.

Also similarly, a sulfuric acid/hydrocarbon emulsion 138 exiting the third sulfuric acid alkylation reactor is directed to an inlet of the third settling chamber of the segmented sulfuric acid settler. In the segmented sulfuric acid settler, a hydrocarbon phase is allowed to separate from a sulfuric acid phase of the sulfuric acid/hydrocarbon emulsion. The sulfuric acid phase exiting an outlet of the third settling chamber is recycled to the third sulfuric acid alkylation reactor as the sulfuric acid recycle stream 140. The hydrocarbon phase from the third settling chamber rises above the settling chambers to be combined with hydrocarbon phases from the first and second settling chambers to form the hydrocarbon effluent stream 112. A portion of the sulfuric acid phase 141 exiting the outlet of the third settling chamber becomes spent acid to be purged and is directed to the acid blowdown section as shown in FIG. 14.

The alkylation process as shown in FIGS. 7 and 8 utilizes an effluent refrigeration system to remove the heat of reaction and control the reaction temperature. The hydrocarbon effluent stream 112 is split into three streams 135, 136 and 137. A portion of the hydrocarbon effluent 137 is introduced into a tube bundle (not shown) in the first sulfuric acid alkylation reactor. The pressure of the hydrocarbon effluent 137 is reduced. As a result, a portion of the hydrocarbon effluent is flashed, and the temperature of the hydrocarbon effluent is reduced. Additional vaporization occurs in the reactor tube bundle (not shown) as the hydrocarbon effluent stream removes the heat of reaction. The two-phase hydrocarbon effluent stream 113 exits the first sulfuric acid alkylation reactor to join the two-phase hydrocarbon effluent streams 134 and 143 from the second and the third sulfuric acid alkylation reactors respectively to form a two-phase hydrocarbon effluent stream 114 which is directed to the refrigeration section as shown in FIG. 9.

Similarly, a portion of the hydrocarbon effluent 136 is introduced into the tube bundle (not shown) in the second sulfuric acid alkylation reactor. Similar to the hydrocarbon effluent 137 above, the hydrocarbon effluent 136 is partially vaporized as it flows through the tube bundle (not shown) to form a two-phase hydrocarbon effluent stream 134. Also similarly, a portion of the hydrocarbon effluent 135 is introduced into the tube bundle (not shown) in the third sulfuric acid alkylation reactor. The hydrocarbon effluent 135 is partially vaporized as it flows through the tube bundle (not shown) to form a two-phase hydrocarbon effluent stream 143.

Figure 9:
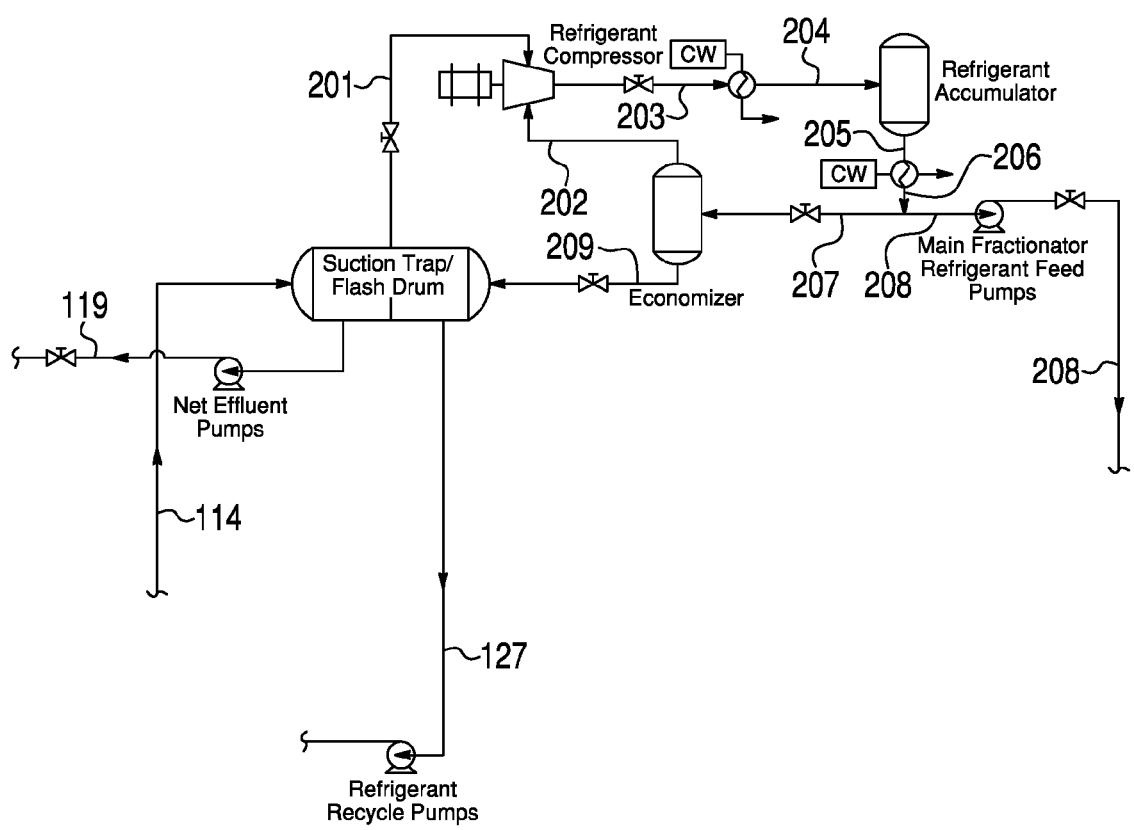
FIG. 9 is a schematic process flow diagram of the refrigeration section of the converted SA alkylation unit of FIG. 7.

FIG. 9 is a schematic process flow diagram of the refrigeration section of the converted SA alkylation unit of FIG. 7. The two-phase hydrocarbon effluent stream 114 from the reaction section as shown in FIG. 8 is introduced into the suction trap side of the suction trap/flash drum separation vessel where the vapor and liquid phases are separated.

Figure 10:
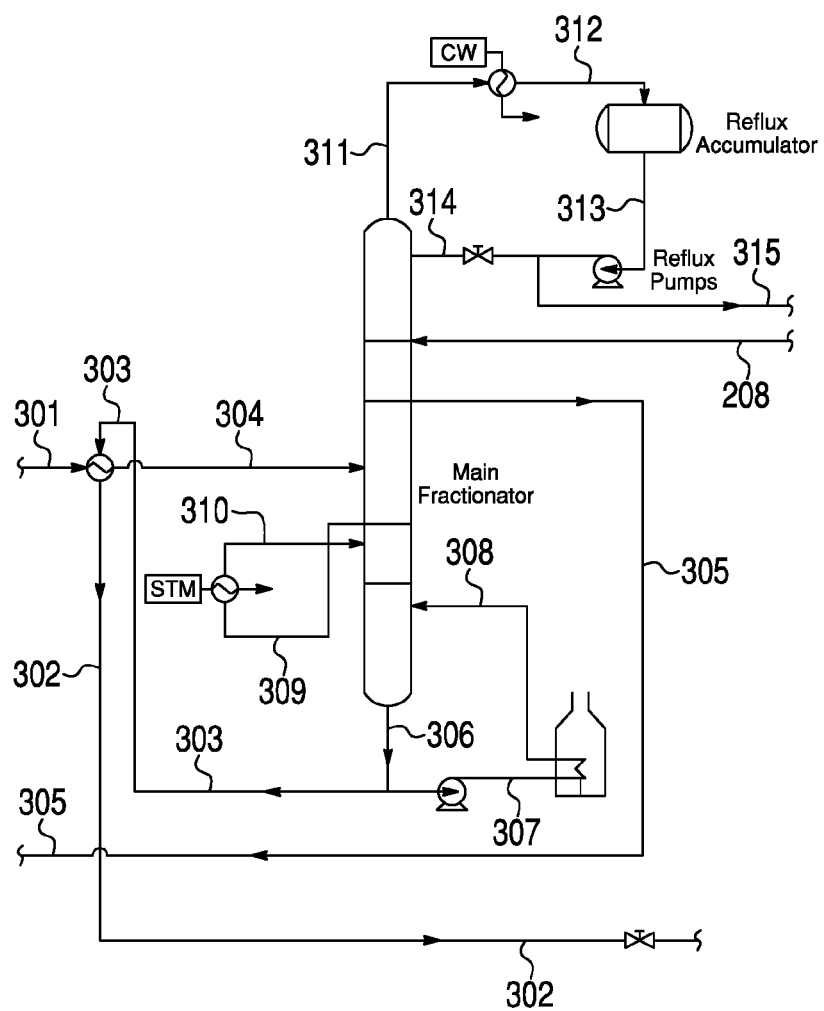
FIG. 10 is a schematic process flow diagram of the main fractionation section of the converted SA alkylation unit of FIG. 7.

The vapor stream 201 from the suction trap/flash drum is compressed by a refrigerant compressor and then condensed in a refrigerant condenser cooled by cooling water. In some embodiments, the refrigerant condenser can also be cooled by other cooling agents such as air. The refrigerant condensate 204 is collected in a refrigerant accumulator. A portion of the refrigerant condensate 208 is directed to the main fractionation section as shown in FIG. 10. The remaining refrigerant condensate 207 is flashed across a control valve and sent to an economizer.

The economizer vapor 202 flows to the refrigerant compressor. The economizer liquid 209 is flashed across a control valve and sent to the flash drum side of the suction trap/flash drum separation vessel. In some embodiments, an economizer is not used and the remaining refrigerant condensate 207 is flashed across a control valve and sent to the flash drum side of the suction trap/flash drum separation vessel. A refrigerant recycle stream 127 comprising isobutane exits from the bottom of the flash drum side of the suction trap/flash drum separation vessel and is sent to the reaction section as shown in FIG. 8 by a refrigerant recycle pump. A net effluent stream 119 comprising alkylate, remaining isobutane and sulfur-containing contaminants exits from the bottom of the suction trap side of the suction trap/flash drum separation vessel and is sent to the reaction section as shown in FIG. 8 by a net effluent pump to cool the hydrocarbon feed streams in the reaction section.

FIG. 10 is a schematic process flow diagram of the main fractionation section (part of the fractionation section) of the converted SA alkylation unit of FIG. 7. The main fractionator 40 as shown in FIG. 1 in the HF alkylation unit is retained or modified to provide a main fractionator in this converted SA alkylation unit. The purified net effluent stream 301 from the net effluent treatment section as shown in FIG. 13 is heated prior to entry into the main fractionator by passing the purified net effluent stream 301 through a heat exchanger wherein a portion of a bottom stream 303 from the main fractionator passing through that heat exchanger is cooled. The heated purified net effluent stream 304 is introduced into the main fractionator.

A new nozzle (not shown) is added to the main fractionator above the isobutane fraction outlet for the side draw 305 to receive the portion of the refrigerant condensate 208 comprising propane from the refrigeration section into the main fractionator, which allows for a refrigeration system propane purge. In some embodiments, no new nozzle is added to the main fractionator above the isobutane fraction outlet for the side draw 305, and the portion of the refrigerant condensate 208 comprising propane from the refrigeration section is added to the purified net effluent stream 301 to be fed into the main fractionator. The top stream 311 comprising propane is cooled in a condenser cooled by cold water. In some embodiments, the condenser can also be cooled by other cooling agents such as air. The cooled top stream 312 is collected in a reflux accumulator. A portion of the cooled top stream comprising primarily propane is directed back into the main fractionator through propane reflux stream 314 by using a reflux pump. The remainder of the cooled top stream 315 is sent to a propane treatment section as shown in FIG. 11.

Figure 12:
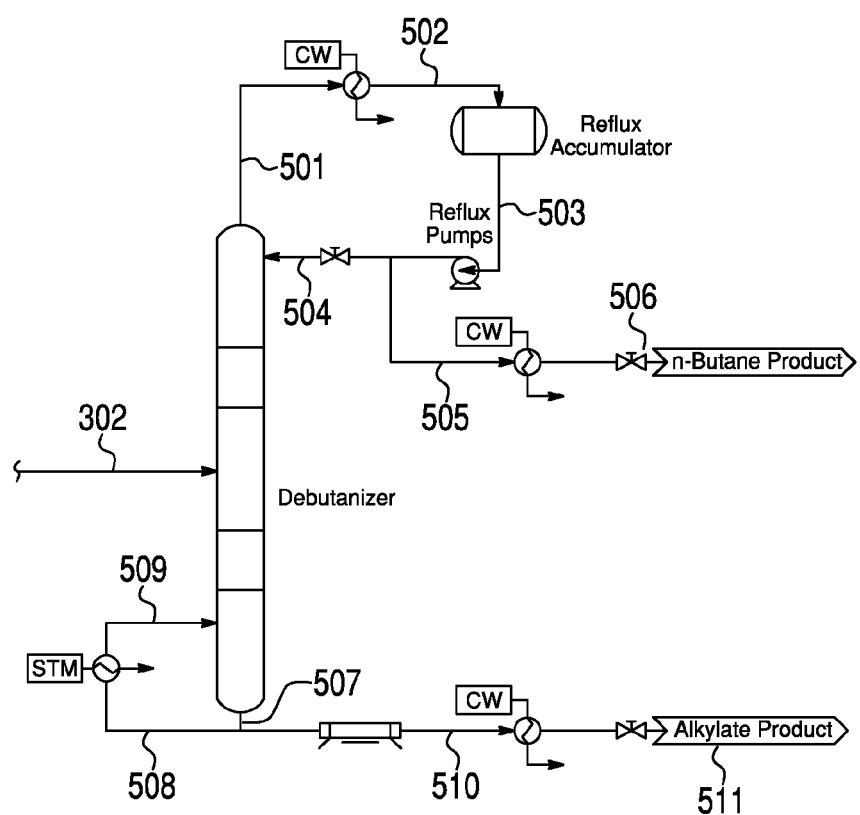
FIG. 12 is a schematic process flow diagram of the debutanizer section of the converted SA alkylation unit of FIG. 7.

An isobutane fraction exits the main fractionator through the side draw 305. The isobutane fraction is directed to a heat exchanger located in the net effluent treatment section as shown in FIG. 13. The isobutane fraction passing through the heat exchanger becomes the recycle isobutane stream 115 which is sent to the reaction section as shown in FIG. 8. A bottom stream 306 from the main fractionator comprises primarily alkylate and n-butane. A portion of the bottom stream 303 is cooled by passing through a heat exchanger to transfer heat to the purified net effluent stream 301. The cooled bottom stream 302 is sent to the debutanizer section as shown in FIG. 12.

Figure 11:
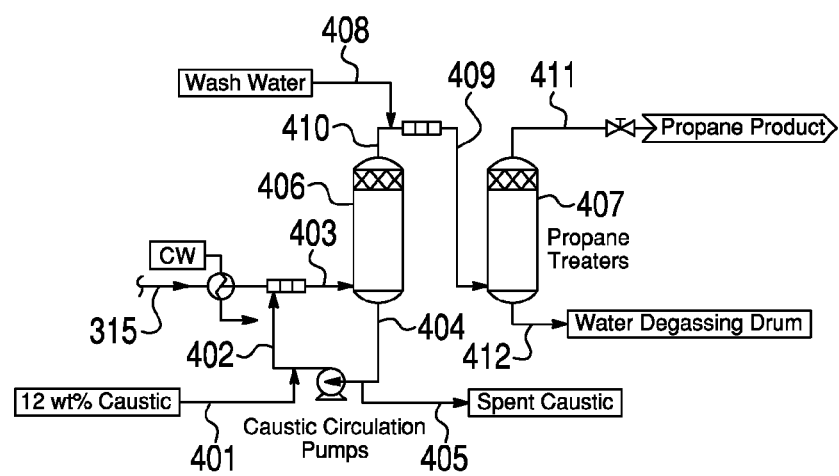
FIG. 11 is a schematic process flow diagram of the propane treatment section of the converted SA alkylation unit of FIG. 7.

FIG. 11 is a schematic process flow diagram of the propane treatment section of the converted SA alkylation unit of FIG. 7. The propane defluorinator 66 as shown in FIG. 1 in the HF alkylation unit is retained or modified to provide propane treaters 406 and 407 in this converted SA alkylation unit. The propane KOH treater 68 as shown in FIG. 1 in the HF alkylation unit is decommissioned.

The remainder of the cooled top stream 315 comprising propane and sulfur dioxide ($SO_2$) impurity is received by a propane treatment section as shown in FIG. 11. The cooled top stream 315 is further cooled by a cold water heat exchanger and then contacted with strong caustic (10-12 wt %) 402 in an in-line static mixer. The resulting mixture 403 is sent to the propane treater 406. The caustic stream 404 can be recycled with a caustic circulation pump. Fresh caustic 401 can be added to the circulation. A caustic slipstream 405 can be purged as spent caustic. In some embodiments, the caustic is an aqueous sodium hydroxide (NaOH) solution.

The caustic washed propane stream 410 is contacted with wash water 408 in an in-line static mixer, and the resulting mixture 409 is sent to the propane treater 407 wherein propane liquid phase is separated from the wash water. The water effluent 412 is sent to a water degassing drum. The purified propane product 411 is recovered from the top of the propane treater 407.

FIG. 12 is a schematic process flow diagram of the debutanizer section (another part of the fractionation section) of the converted SA alkylation unit of FIG. 7. The cooled bottom stream 302 comprising alkylate and n-butane is introduced into a fractionation column (debutanizer) to separate out n-butane from alkylate. The top stream 501 comprising n-butane is cooled in a condenser cooled by cold water. In some embodiments, the condenser can also be cooled by other cooling agents such as air. The cooled top stream 502 is collected in a reflux accumulator. A portion of the cooled top stream comprising primarily n-butane is directed back into the debutanizer through n-butane reflux stream 504 by using a reflux pump. The remainder of the cooled top stream 505 is further cooled and recovered as n-butane product 506. The bottom stream 507 comprising alkylate is cooled and recovered as an alkylate product 511.

FIG. 13 is a schematic process flow diagram of the net effluent treatment section of the converted SA alkylation unit of FIG. 7. In some embodiments, an HF acid recontactor (not shown) is used in an HF alkylation unit to remove residual HF from the hydrocarbon effluent stream 37 as shown in FIG. 1. Such HF acid recontactor can be retained or modified to provide a sulfuric acid coalescer to remove the residual sulfuric acid phase (sulfur-containing contaminants) from the net effluent in this converted SA alkylation unit.

The heated net effluent 120 comprising alkylate, remaining isobutane and sulfur-containing contaminants is fed to a sulfuric acid coalescer (Acid Coalescer in FIG. 13) to remove the sulfur-containing contaminants from the net effluent. The resulting net effluent 601 is further purified in a dry alumina adsorption vessel. The purified net effluent stream 602 passes through a heat exchanger and is sent to the main fractionation section as shown in FIG. 10 as the purified net effluent stream 301. The isobutane fraction 305 from the main fractionator as shown in FIG. 10 passes through the heat exchanger and is sent to the reaction section as shown in FIG. 8 as the recycle isobutane stream 115.

FIG. 14 is a schematic process flow diagram of the acid blowdown section of the converted SA alkylation unit of FIG. 7. The HF acid relief neutralizer 91 as shown in FIG. 1 in the HF alkylation unit can be retained or modified to provide a blowdown vapor scrubber in this converted SA alkylation unit. In some embodiments, a remote HF storage tank (not shown in FIG. 1) can be retained or modified to provide a sulfuric acid blowdown drum (Acid Blowdown Drum in FIG. 14) in this converted SA alkylation unit. In some embodiments, the ASO/KOH separator 83 as shown in FIG. 1 in the HF alkylation unit can be retained or modified to provide a sulfuric acid blowdown drum in this converted SA alkylation unit. In some embodiments, an HF blowdown drum (not shown in FIG. 1) can be retained or modified to provide a sulfuric acid blowdown drum in this converted SA alkylation unit.

A portion of the sulfuric acid phase 141 exiting the outlet of the third settling chamber is introduced into a sulfuric acid blowdown drum as spent acid to be purged. Residual hydrocarbons contained in the spent acid can be flashed in the sulfuric acid blowdown drum to form a hydrocarbon vapor. An acidic vapor effluent 703 comprising hydrocarbons from the sulfuric acid blowdown drum is sent to a blowdown vapor scrubber wherein the acidic vapor is contacted with a circulating caustic solution 706. In some embodiments, the caustic solution is an aqueous sodium hydroxide (NaOH) solution. Liquid hydrocarbons 702 are recovered at the bottom of one side of the sulfuric acid blowdown drum and sent to the reaction section through a recovered hydrocarbon pump. Spent acid 701 is recovered at the bottom of the other side of the sulfuric acid blowdown drum and sent to a spent acid storage through a spent acid pump.

The acidic vapor effluent 703 is scrubbed by the caustic solution in the blowdown vapor scrubber. Another acidic vapor stream 708 comprising hydrocarbons from a sulfuric acid relief (flare) header is also introduced into the blowdown vapor scrubber to be scrubbed therein. A hydrocarbon stream 707 comprising hydrocarbons exits the blowdown vapor scrubber and is directed to an HC relief (flare) header. A portion of the caustic solution 705 from the bottom of the blowdown vapor scrubber can be recycled with a caustic circulation pump. Fresh caustic solution 704 can be added to the circulation. A caustic slipstream 710 can be purged as spent caustic.

The present disclosure provides a method for converting a hydrogen fluoride alkylation unit which utilizes hydrogen fluoride as a reaction catalyst to a sulfuric acid alkylation unit. The hydrogen fluoride alkylation unit comprises an HF alkylation reactor, an HF alkylation fractionation section comprising at least one fractionator, and an HF acid relief neutralizer vessel. The method comprises: (a) substituting sulfuric acid for hydrogen fluoride as the reaction catalyst; (b) retaining the HF acid relief neutralizer vessel as a blowdown vapor scrubber; (c) retaining the HF alkylation fractionation section as a sulfuric acid alkylation fractionation section; (d) providing at least one sulfuric acid alkylation reactor; (e) providing a refrigeration section comprising a refrigerant compressor and a heat exchanger for condensing a vapor stream from the refrigerant compressor; (f) providing a conduit for recycling an isoparaffin comprising isobutane from the refrigeration section to said at least one sulfuric acid alkylation reactor; and (g) providing a feed/effluent heat exchanger for cooling a hydrocarbon feed stream and heating a net effluent stream. In some embodiments, the HF alkylation unit is a gravity-flow HF alkylation unit (Phillips HF alkylation unit). In some embodiments, the HF alkylation unit is a pumped-flow HF alkylation unit (UOP HF alkylation unit). In some embodiments, the HF alkylation reactor is decommissioned, and at least one new sulfuric acid alkylation reactor is added or provided to the converted SA alkylation unit.

In some embodiments, the HF alkylation unit further comprises a feed dryer, and one or more feed dryers in the existing HF alkylation unit can be retained or modified to provide one or more feed dryers in a converted SA alkylation unit. Feed dryers are used to dry hydrocarbons such as olefin and isoparaffin in hydrocarbon feed streams to an alkylation reactor. In some embodiments, a drying agent such as activated alumina is provided to be used in the feed dryer for the converted SA alkylation unit. The drying agent from an existing HF alkylation unit can be retained, reused or replaced. In some embodiments, one or more feed dryers in an existing HF alkylation unit can be decommissioned.

In some embodiments, the HF alkylation unit further comprises one or more feed coalescers, and said one or more feed coalescers are retained or modified to provide one or more feed coalescers upstream of the one or more feed dryers respectively in a converted SA alkylation unit. The feed coalescers are used to remove suspended water droplets entrained in a hydrocarbon stream. In some embodiments, a coalescing media is provided to be used in a feed coalescer for the converted SA alkylation unit. The coalescing media from an existing HF alkylation unit can be retained, reused or replaced. In some embodiments, one or more feed coalescers in an existing HF alkylation unit can be decommissioned.

In some embodiments, the HF alkylation unit further comprises an HF acid cooler, and the HF acid cooler is decommissioned. In some embodiments, the HF alkylation unit further comprises an HF storage tank under the vertical HF acid settler, and the HF storage tank under the vertical HF acid settler is decommissioned. In some embodiments, the HF alkylation unit further comprises an HF regenerator, and the HF regenerator is decommissioned. In some embodiments, the HF alkylation unit further comprises an HF regenerator condenser, and the HF regenerator condenser is decommissioned. In some embodiments, the HF alkylation unit further comprises an HF regenerator isobutane superheater, and the HF regenerator isobutane superheater is decommissioned. In some embodiments, the HF alkylation unit further comprises an HF regenerator overhead pump, and the HF regenerator overhead pump is decommissioned.

In some embodiments, one or more feed/effluent heat exchangers are added or provided in a converted SA alkylation unit to reduce the temperature of hydrocarbon feed streams and increase the temperature of net effluent streams. In some embodiments, a feed/effluent heat exchanger is located downstream from the feed dryer and upstream of the SA alkylation reactor with respect to the flow direction of the hydrocarbon feed stream. In some embodiments, one or more new feed/effluent heat exchangers are added or provided in a converted SA alkylation unit. In some embodiments, the feed/effluent heat exchanger is a shell and tube heat exchanger.

In some embodiments, at least one new sulfuric acid alkylation reactor is added or provided in a converted SA alkylation unit. In some embodiments, the sulfuric acid alkylation reactor is an internally agitated sulfuric acid alkylation reactor, and at least one internally agitated sulfuric acid alkylation reactor is added or provided in a converted SA alkylation unit. In some embodiments, the at least one new sulfuric acid alkylation reactor or the at least one new internally agitated sulfuric acid alkylation reactor replaces one or more HF acid coolers in an existing HF alkylation unit. The term "internally agitated sulfuric acid alkylation reactor", as used herein, means a sulfuric acid alkylation reactor in which hydrocarbons and sulfuric acid are internally agitated inside the reactor to form a mixture or an emulsion to create the necessary interfacial area for alkylation reactions. The agitation can be realized using well-known chemical engineering practice. In some embodiments, a rotating mixer such as an impeller is used to generate agitation. In some embodiments, static reactor internals are used to generate agitation. In some embodiments, one or more static mixers are used to generate agitation. In some embodiments, a static contacting media is used to generate agitation. In some embodiments, the internally agitated sulfuric acid alkylation reactor is a horizontal SA alkylation reactor such as a DuPont STRATCO© Contactor™ reactor which is generally disclosed in U.S. Pat. Nos. 3,759,318 and 9,580,366, both are herein incorporated by reference in their entirety for all purposes. In some embodiments, the internally agitated sulfuric acid alkylation reactor is a vertical SA alkylation reactor which, for example, is disclosed in U.S. Pat. No. 7,850,929 which is incorporated herein by reference in its entirety for all purposes.

In some embodiments, no emulsion pump is added or provided to the converted SA alkylation unit to emulsify or mix a sulfuric acid recycle stream with a hydrocarbon feed stream, and all sulfuric acid/hydrocarbon emulsion exiting a reaction zone is sent to a SA settler to separate the hydrocarbon phase from the SA phase. A pumped-flow HF alkylation unit (UOP HF alkylation unit) typically comprises one or more HF acid circulation pumps to circulate the HF acid recycle stream within the reaction section. In some embodiments, no HF acid circulation pump is retained from an HF alkylation unit as an emulsion pump for the converted SA alkylation unit. In some embodiments, the one or more HF acid circulation pumps in an existing HF alkylation unit are decommissioned. In some embodiments, the converted SA alkylation unit comprises no emulsion pump for emulsifying or mixing a sulfuric acid recycle stream with a hydrocarbon feed stream.

In some embodiments, the sulfuric acid alkylation reactor is an externally agitated sulfuric acid alkylation reactor, and at least one new externally agitated sulfuric acid alkylation reactor is added or provided in a converted SA alkylation unit. The term "externally agitated sulfuric acid alkylation reactor", as used herein, means a sulfuric acid alkylation reactor where hydrocarbons and sulfuric acid are externally agitated outside the reactor to form a mixture or an emulsion to create the necessary interfacial area for alkylation reactions. The agitation can be realized using a homogenizer such as a rotor stator mixer or a static mixer, and the generated emulsion can be introduced into the reactor.

In some embodiments, a refrigeration section is added or provided in a converted SA alkylation unit to satisfy the lower reaction temperature requirement comparing with an HF alkylation unit. The refrigeration section is fluidly connected with the reaction section or a SA alkylation reactor therein to receive a hydrocarbon stream comprising isoparaffin (e.g., isobutane) from the reaction section or the SA alkylation reactor and recycle at least a portion of the isoparaffin contained in the hydrocarbon stream to the reaction section or the SA alkylation reactor in the form of a refrigerant recycle stream (FIG. 4). In some embodiments, the refrigeration section receives and separates a hydrocarbon effluent stream from a SA alkylation reactor to generate hydrocarbon streams comprising a refrigerant recycle stream comprising isoparaffin (e.g., isobutane) and a net effluent stream comprising alkylate, remaining isoparaffin (e.g., isobutane) and sulfur-containing contaminants. In some embodiments, the refrigeration section receives a vapor stream comprising isoparaffin (e.g., isobutane) from a SA alkylation reactor and compresses and condenses the vapor stream to form a refrigerant recycle stream. At least a portion of the refrigerant recycle stream comprising isoparaffin (e.g., isobutane) is recycled to the SA alkylation reactor.

The refrigeration section typically comprises a refrigerant compressor and a heat exchanger (condenser, refrigerant condenser, or compressor condenser) for condensing a vapor stream from the refrigerant compressor. In some embodiments, the refrigeration section further comprises a compressor K/O (knockout) drum upstream of the refrigerant compressor to remove suspended liquid droplets entrained in a vapor stream before the vapor stream is introduced into the refrigerant compressor.

In some embodiments, the refrigeration section further comprises a liquid-vapor separation zone where the liquid-vapor separation is effected. Such liquid-vapor separation zone is upstream of the compressor K/O drum (if present) and the refrigerant compressor. In some embodiments, the liquid-vapor separation zone comprises a two-compartment (suction trap and flash drum) separation vessel with a common vapor space. The vapor phase comprising light hydrocarbon such as unreacted isoparaffin (e.g., isobutane), n-butane and propane is compressed in the refrigerant compressor and then condensed in the condenser which can be cooled by a cooling agent such as cooling water or air.

In some embodiments, the refrigeration section further comprises an economizer (compressor economizer). In some embodiments, refrigerant condensate can be flashed and sent to the economizer. The economizer vapor flows to an intermediate stage of the refrigerant compressor. The economizer liquid can be flashed and sent to the flash drum side of the suction trap/flash drum. In some embodiments, the refrigeration section further comprises a refrigerant accumulator vessel which can be used to collect the refrigerant condensate. In some embodiments, the refrigeration section further comprises a heat exchanger which can be used to cool a liquid stream from the refrigerant accumulator.

In some embodiments, the equipment or vessel(s) provided in the refrigeration section are new equipment or vessel(s). In some embodiments, a new refrigerant compressor is provided for the refrigeration section in the converted SA alkylation unit. In some embodiments, a new compressor K/O drum is provided for the refrigeration section in the converted SA alkylation unit. In some embodiments, a new refrigerant condenser for condensing a vapor stream from the refrigerant compressor is provided for the refrigeration section in the converted SA alkylation unit. In some embodiments, a new refrigerant recycle pump is provided for the refrigeration section in the converted SA alkylation unit. In some embodiments, a new refrigerant accumulator vessel is provided for the refrigeration section in the converted SA alkylation unit. In some embodiments, a new suction trap/flash drum separation vessel is provided for the refrigeration section in the converted SA alkylation unit.

In some embodiments, the existing HF alkylation unit further comprises a fractionator (e.g., isostripper) receiver acting as a surge drum for the isobutane recycle pump. Such fractionator receiver can be retained or modified to provide a refrigerant accumulator vessel for the refrigeration section in the converted SA alkylation unit.

In some embodiments, a conduit is added to or provided in a converted SA alkylation unit to recycle an isoparaffin comprising isobutane (recycle isobutane) from the refrigeration section to the at least one sulfuric acid alkylation reactor. In some embodiments, a conduit is added to or provided in a converted SA alkylation unit to connect a refrigerant recycle pump with the at least one sulfuric acid alkylation reactor or the reaction section. The refrigerant recycle pump is used to send the refrigerant recycle stream to the at least one sulfuric acid alkylation reactor or the reaction section. In some embodiments, the isoparaffin comprising isobutane exits from the bottom of the flash drum side of the suction trap/flash drum separation vessel as a refrigerant recycle stream and is sent to the reaction section or the at least one sulfuric acid alkylation reactor by the refrigerant recycle pump.

In alkylation, a large recycle flow of isobutane to the reaction section is required to promote the desirable alkylation reaction and suppress polymerization reactions that can negatively impact acid consumption and alkylate quality. As shown in FIGS. 3 and 4, in an HF alkylation unit, all of this isobutane recycle flow is from the fractionation section, while in a converted SA alkylation unit, in some embodiments, only about 50% of the isobutane flow is from the fractionation section and the other 50% is from the refrigeration section. Therefore, it is possible to double the effective capacity of the alkylation unit without requiring significant changes to the fractionation section equipment, making the conversion more cost-effective.

In some embodiments, the amount of the isobutane recycled from the refrigeration section to the reaction section in a converted SA alkylation unit ranges from about 30% to about 70% comparing with the total amount of isobutane recycled from both the refrigeration section and the fractionation section to the reaction section. In some embodiments, the amount of the isobutane recycled from the refrigeration section to the reaction section in a converted SA alkylation unit ranges from about 40% to about 60% comparing with the total amount of isobutane recycled from both the refrigeration section and the fractionation section to the reaction section.

In some embodiments, after converting an HF alkylation unit to a SA alkylation unit, the capacity of the converted SA alkylation unit is increased by at least 50% comparing with the capacity of the HF alkylation unit. In some embodiments, the capacity is increased by at least 75%. In some embodiments, the capacity is increased by at least 100%. In some embodiments, the capacity is increased by at least 125%.

In some embodiments, the HF alkylation fractionation section is retained or modified to provide a sulfuric acid alkylation fractionation section in a converted SA alkylation unit. In some embodiments, the existing HF alkylation unit comprises a fractionation section comprising a main fractionator and a debutanizer, and in some embodiments, a nozzle is added to the main fractionator above the isobutane fraction outlet for the side draw (where the isobutane fraction exits the fractionation column) to provide a feed stream comprising the refrigerant condensate from the refrigeration section, which allows for a refrigeration system propane purge.

The fractionation section in a converted SA alkylation unit or an existing HF alkylation unit can have several different configurations or designs. In one configuration, the fractionation section comprises a single main fractionator which generates a propane fraction, an isobutane fraction, a normal butane (n-butane) fraction, and an alkylate fraction. In another configuration, the fractionation section comprises two fractionators. The first fractionator (e.g., main fractionator or depropanizer) generates a propane fraction, an isobutane fraction, and a bottom fraction comprising n-butane and alkylate. The bottom fraction is sent to the second fractionator (e.g., debutanizer) which generates a n-butane fraction and an alkylate fraction. In another configuration, the fractionation section comprises two fractionators. The first fractionator (e.g., main fractionator) generates a top fraction comprising propane and isobutane, an isobutane fraction, a n-butane fraction, and an alkylate fraction. The top fraction is sent to the second fractionator (e.g., depropanizer) which generates a propane fraction and an isobutane fraction. In another configuration, the fractionation section comprises two fractionators. The first fractionator (e.g., depropanizer) generates a propane fraction, an isobutane fraction, and a bottom fraction comprising isobutane, n-butane and alkylate. The bottom fraction is sent to the second fractionator (e.g., isostripper) which generates an isobutane fraction, a n-butane fraction and an alkylate fraction. In some embodiments, approximately 50% of the HF acid settler effluent is sent to the first fractionator (e.g., depropanizer) which generates a propane fraction, an isobutane fraction, and a bottom fraction comprising isobutane, n-butane and alkylate. The bottom fraction is sent to the second fractionator (e.g., isostripper) along with the remaining HF acid settler effluent to generate an isobutane fraction, a n-butane fraction and an alkylate fraction. In some embodiments, the HF alkylation fractionation section is retained or modified to provide a sulfuric acid alkylation fractionation section in a converted SA alkylation unit, and the HF alkylation fractionation section and the sulfuric acid alkylation fractionation section have same configuration, that is, the configuration of the HF alkylation fractionation section is retained in the conversion process.

In some embodiments, the HF acid relief neutralizer vessel in an existing HF alkylation unit is retained or modified to provide a blowdown vapor scrubber in a converted SA alkylation unit. The blowdown vapor scrubber in a converted SA alkylation unit is used to neutralize any acidic vapors from the unit before they go to the relief (flare) header to prevent corrosion in the relief (flare) piping. In some embodiments, an aqueous KOH solution is used in the HF acid relief neutralizer vessel for neutralization, and the conversion method further comprises substituting NaOH for KOH to be used as a caustic solution in the blowdown vapor scrubber to neutralize acidic vapors.

In some embodiments, the existing HF alkylation unit further comprises an HF alkylation waste treatment system comprising an HF acid neutralization pit, and said HF acid neutralization pit is retained or modified to provide a sulfuric acid neutralization basin in a sulfuric acid alkylation waste treatment system in the converted SA alkylation unit. The sulfuric acid neutralization basin is used to neutralize an acidic hydrocarbon drain or a sulfuric acid drain which may originate from an equipment such as a pump, a heat exchanger, a drum, or a vessel which needs to be drained of acidic hydrocarbon and/or sulfuric acid for maintenance or repair. Typically, a caustic solution (e.g., NaOH) is used as the neutralizing agent. In some embodiments, the caustic solution used in the blowdown vapor scrubber can be shared with the sulfuric acid neutralization basin. In some embodiments, a portion of the caustic solution from the bottom of the blowdown vapor scrubber can be introduced into the sulfuric acid neutralization basin. In some embodiments, the caustic solution is an aqueous NaOH solution. In some embodiments, an aqueous KOH solution is used in the HF acid neutralization pit, and the conversion method further comprises substituting NaOH for KOH to be used in the sulfuric acid neutralization basin to neutralize acidic hydrocarbon and/or sulfuric acid. The term "acidic hydrocarbon", as used herein, means a hydrocarbon stream containing sulfuric acid.

In some embodiments, the existing HF alkylation unit further comprises at least one propane defluorinator, and said at least one propane defluorinator is retained or modified to provide at least one propane purification vessel in the converted SA alkylation unit. In some embodiments, there are two or more propane defluorinators in an existing HF alkylation unit. One of such propane defluorinator can be retained or modified to provide a caustic wash vessel (e.g., propane treater 406 in FIG. 11) to purify the propane product in the converted SA alkylation unit. In some embodiments, the caustic solution used in the blowdown vapor scrubber can be directed to such caustic wash vessel. Another propane defluorinator can be retained or modified to provide a water wash vessel (e.g., propane treater 407 in FIG. 11) to purify the propane product in the converted SA alkylation unit. Typically, the water wash vessel is downstream from the caustic wash vessel.

In some embodiments, the existing HF alkylation unit further comprises an HF alkylation propane stripper, and said HF alkylation propane stripper is decommissioned. Typically, an HF alkylation propane stripper is a small reboiled stripping column utilizing steam as the heating medium. It is used to recover HF present in a propane product stream.

In some embodiments, the existing HF alkylation unit further comprises an HF acid recontactor, and said HF acid recontactor is retained or modified to provide a sulfuric acid coalescer (e.g., the acid coalescer in FIG. 13) in the converted SA alkylation unit. The sulfuric acid coalescer is used to remove sulfuric acid from a hydrocarbon stream such as a net effluent. In some embodiments, the sulfuric acid coalescer comprises a coalescing media inside. In some embodiments, the HF acid recontactor is decommissioned.

In some embodiments, the existing HF alkylation unit further comprises a propane KOH treater and/or a n-butane KOH treater, and said propane KOH treater and/or said n-butane KOH treater is retained or modified to provide a net effluent purification vessel for removing sulfur-containing contaminants from the net effluent in the converted SA alkylation unit. In some embodiments, the net effluent purification vessel is a dry alumina adsorption vessel (e.g., the dry alumina adsorption in FIG. 13) containing dry alumina (e.g., activated alumina) to adsorb or remove sulfur-containing contaminants from the net effluent. In some embodiments, the net effluent purification vessel contains a purifying agent comprising an adsorbent selected from the group consisting of alumina, bauxite, aluminosilicate, zeolite, inorganic silicates, zinc oxide, and combinations thereof. In some embodiments, a sulfuric acid coalescer is upstream of the net effluent purification vessel with respect to the net effluent flow direction. In some embodiments, the propane KOH treater is decommissioned. In some embodiments, the n-butane KOH treater is decommissioned. In some embodiments, a new dry alumina adsorption vessel is provided to the converted SA alkylation unit. In some embodiments, the propane KOH treater and/or the n-butane KOH treater in the HF alkylation unit is retained or modified to provide propane treater(s) in the converted SA alkylation unit to purify propane product.

In some embodiments, the existing HF alkylation unit further comprises an alumina treater to remove residual HF acid in the propane product stream and/or the n-butane product stream, and said alumina treater is retained or modified to provide a dry alumina adsorption vessel in the converted SA alkylation unit.

When a dry alumina adsorption vessel containing dry alumina is used to purify the net effluent, the resulting net effluent is dry. The isobutane recycle stream separated out from the dry net effluent in a fractionator is also dry. In such embodiments, a converted SA alkylation unit can operate without feed dryer(s) and/or feed coalescer(s) since a SA alkylation reaction is relatively insensitive to the small amount of water contained in the olefin feed and makeup isobutane. Also in such embodiments, the olefin feed flowrate can be increased for the capacity expansion of the unit without requiring any modification to the existing feed dryer(s). In some embodiments, with a dry isobutane recycle, the existing feed dryer(s) and/or feed coalescer(s) can be decommissioned. In some embodiments, the existing feed dryer(s) and/or feed coalescer(s) can be retained to remove the relatively small amount of water in the olefin feed stream to further decrease the sulfuric acid consumption in the alkylation process.

In some embodiments, a new sulfuric acid settler is provided as a sulfuric acid settler for the converted SA alkylation unit. In some embodiments, a new sulfuric acid settler is provided as a segmented sulfuric acid settler as disclosed in this disclosure for the converted SA alkylation unit. In some embodiments, the new sulfuric acid settler is vertical. In some embodiments, a suitable vessel in the HF alkylation unit is retained or modified to provide a sulfuric acid settler for the converted SA alkylation unit. In some embodiments, the HF alkylation unit further comprises an HF acid settler, and the HF acid settler is retained or modified to provide a sulfuric acid settler for the converted SA alkylation unit. In some embodiments, the HF acid settler is vertical, and the vertical HF acid settler is retained or modified to provide a vertical sulfuric acid settler. In some embodiments, the vertical HF acid settler is retained or modified to provide a segmented sulfuric acid settler as disclosed in this disclosure. In some embodiments, the HF acid settler is decommissioned.

In some embodiments, the sulfuric acid settler is empty inside, that is, the sulfuric acid settler has no internal components. In some embodiments, the sulfuric acid settler comprises at least one coalescing media. In some embodiments, the sulfuric acid settler is vertical and its bottom section is segmented into two or more settling chambers. In some embodiments, the sulfuric acid settler is a segmented sulfuric acid settler as disclosed in this disclosure. In some embodiments, the sulfuric acid settler is sufficient to separate the hydrocarbon phase from the sulfuric acid phase, and the converted SA alkylation unit comprises no sulfuric acid after settler or secondary sulfuric acid settler downstream of the sulfuric acid settler for further separation.

In some embodiments, the at least one sulfuric acid alkylation reactor comprises an acid settling zone inside the reactor vessel, and the converted sulfuric acid alkylation unit comprises no sulfuric acid settler other than the acid settling zone inside the reactor vessel. In such embodiments, the HF acid settler can be decommissioned.

In some embodiments, the existing HF alkylation unit further comprises a remote HF storage tank, and said remote HF storage tank is retained or modified to provide a sulfuric acid blowdown drum (e.g., acid blowdown drum in FIG. 14) or a spent acid aftersettler in the converted SA alkylation unit. In some embodiments, the remote HF storage tank is retained or modified to provide a spent acid aftersettler located upstream of the sulfuric acid blowdown drum and downstream from the sulfuric acid settler or the outlet of the final settling chamber of a segmented sulfuric acid settler. The spent acid aftersettler is used to further separate the hydrocarbon phase or remove the residual hydrocarbons from the sulfuric acid phase. In some embodiments, the remote HF storage tank is retrofitted to provide the sulfuric acid blowdown drum by installing a vertical baffle in the tank to separate the acid and hydrocarbon zones. In some embodiments, an HF storage tank or a remote HF storage tank can be retained or modified to provide a sulfuric acid settler.

In some embodiments, the existing HF alkylation unit further comprises a remote HF blowdown drum, and said remote HF blowdown drum is retained or modified to provide a sulfuric acid blowdown drum (e.g., acid blowdown drum in FIG. 14) or a spent acid aftersettler in the converted SA alkylation unit. In some embodiments, the remote HF blowdown drum is retained or modified to provide a spent acid aftersettler located upstream of the sulfuric acid blowdown drum and downstream from the sulfuric acid settler or the outlet of the final settling chamber of a segmented sulfuric acid settler. In some embodiments, an HF blowdown drum or a remote HF blowdown drum can be retained or modified to provide a sulfuric acid settler.

In some embodiments, the existing HF alkylation unit further comprises an ASO/KOH separator, and said ASO/KOH separator is retained or modified to provide a sulfuric acid blowdown drum (e.g., acid blowdown drum in FIG. 14) in the converted SA alkylation unit.

Figure 16:
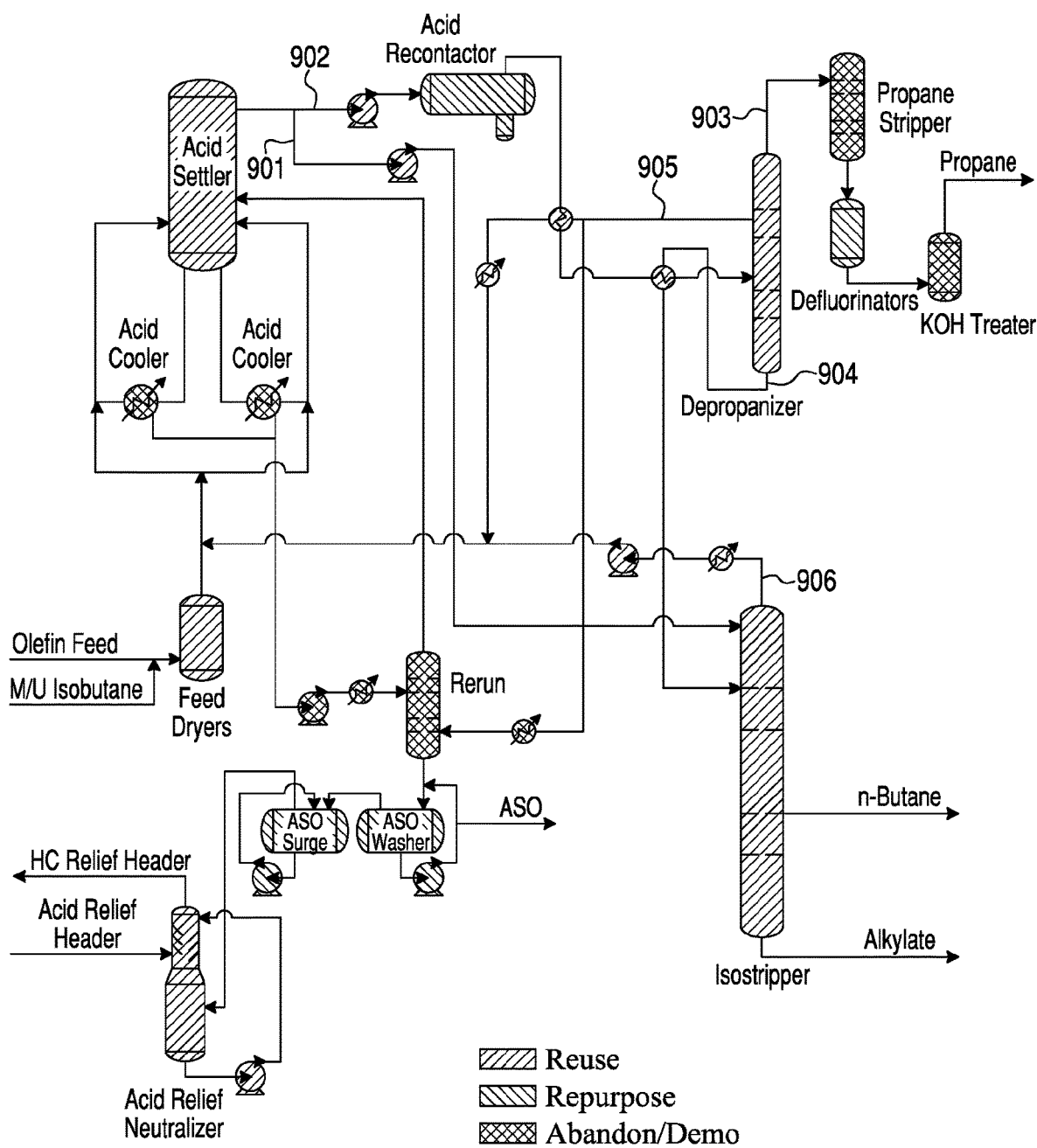
FIG. 16 shows a simplified process flow diagram of an original HF alkylation unit which uses HF as the reaction catalyst to produce alkylate.

In some embodiments, the existing HF alkylation unit further comprises an ASO washer and an ASO surge drum (FIG. 16). The ASO washer washes the acid soluble oil (ASO) with a caustic solution (e.g., an aqueous KOH solution) to neutralize residual HF acid contained therein. The ASO surge drum collects ASO where it is continuously circulated and exported in batch. The ASO needs to be continuously circulated to prevent solidification. In some embodiments, the ASO washer is retained or repurposed as spent acid aftersettler (FIG. 17) in the converted SA alkylation unit to further recover hydrocarbons contained in the spent acid before it is purged. The hydrocarbons separated out in the spent acid aftersettler can exit from an outlet (not shown in FIG. 17) to be recycled to the sulfuric acid alkylation reactor. In some embodiments, the ASO surge drum is retained or repurposed as acid blowdown drum (FIG. 17) in the converted SA alkylation unit.

In some embodiments, the existing HF alkylation unit further comprises a tar neutralizer and a polymer surge drum. The tar neutralizer neutralizes residual HF acid contained in ASO, and the polymer surge drum collects ASO and sends it to the tar neutralizer. In some embodiments, the tar neutralizer is retained. In some embodiments, the tar neutralizer is retained or repurposed as spent acid aftersettler in the converted SA alkylation unit to further recover hydrocarbons contained in the spent acid before it is purged. In some embodiments, the polymer surge drum is retained. In some embodiments, the polymer surge drum is retained or repurposed as acid blowdown drum in the converted SA alkylation unit.

In some embodiments, the existing HF alkylation unit further comprises a n-butane defluorinator and/or a propane defluorinator. In some embodiments, the n-butane defluorinator and/or the propane defluorinator is decommissioned. In some embodiments, the n-butane defluorinator and/or the propane defluorinator is retained or modified to provide a net effluent purification vessel (e.g., the dry alumina adsorption in FIG. 13) for removing sulfur-containing contaminants from the net effluent in the converted SA alkylation unit.

In some embodiments, the existing HF alkylation unit further comprises KOH regeneration facilities. In some embodiments, the KOH regeneration facilities are decommissioned. In some embodiments, the KOH regeneration facilities are retained or modified to provide NaOH or KOH regeneration facilities in the converted SA alkylation unit.

In some embodiments, the existing HF alkylation unit further comprises at least one ASO neutralization vessel. In some embodiments, the at least one ASO neutralization vessel is decommissioned. In some embodiments, the at least one ASO neutralization vessel comprises one or more static mixer(s) (e.g., the static mixer 81 in FIG. 1). In some embodiments, the at least one ASO neutralization vessel can be retained or modified to provide one or more propane purification vessel(s) (e.g., the in-line static mixer(s) in FIG. 11) in the converted SA alkylation unit. In some embodiments, an ASO neutralization vessel is retained or modified to provide a caustic wash vessel (e.g., propane treater 406 in FIG. 11) to purify the propane product in the converted SA alkylation unit. In some embodiments, an ASO neutralization vessel is retained or modified to provide a water wash vessel (e.g., propane treater 407 in FIG. 11) to purify the propane product in the converted SA alkylation unit.

In some embodiments, the vertical HF acid settler in an existing HF alkylation unit is modified to provide a sulfuric acid settler in the converted SA alkylation unit. In some embodiments, the bottom section of the sulfuric acid settler is segmented into two or more settling chambers.

Typically, a vertical HF acid settler comprises a vertical vessel having an outlet at its top section or upper end and in some embodiments at the top of the vertical vessel, a vertical interior wall, a bottom, and internal components comprising an internal baffle extending upwardly from the bottom of the vertical vessel. In some embodiments, the bottom is closed, that is, the bottom is of a gas and/or liquid impermeable material. In some embodiments, the vertical vessel has internal components such as sieve tray decks in the upper portion of the vessel, an internal baffle in the bottom which separates the HF acid rich bottom portion of the vessel into two chambers, and perforated plates at the acid riser (HF alkylation reactor) pipe inlet to the vertical vessel to disperse the incoming liquid (HF/hydrocarbon mixture or emulsion).

The present disclosure provides a method for converting a vertical HF acid settler to a segmented sulfuric acid settler. The vertical HF acid settler comprises a vertical vessel having an outlet at its top section, a vertical interior wall, a bottom, and an internal baffle extending upwardly from the bottom of the vertical vessel. The method comprises: (a) retaining the internal baffle to provide at least one internal vertical wall defining settling chambers within the vessel, said internal vertical wall extending upwardly from the bottom of the vertical vessel; (b) retaining the outlet which is at the top section of the vertical vessel; (c) providing a first coalescing media extending substantially the full diameter of the vertical vessel, the first coalescing media being positioned above the internal vertical wall; and (d) providing an inlet and an outlet for each of said settling chambers, the outlet of a settling chamber being positioned below the inlet of said settling chamber.

In some embodiments, the method further comprises: providing a second coalescing media extending substantially the full diameter of the vertical vessel, the second coalescing media being spaced above the first coalescing media but below the outlet at the top section of the vertical vessel.

In some embodiments, the method further comprises: installing additional one or more internal vertical walls defining additional settling chambers within the vessel, said additional one or more internal vertical walls extending upwardly from the bottom of the vertical vessel and having substantially the same height as the at least one internal vertical wall converted from the internal baffle; and providing an inlet and an outlet for each of said additional settling chambers, the outlet of a settling chamber being positioned below the inlet of said settling chamber.

In some embodiments, the method further comprises: providing an additional outlet at the bottom of at least one settling chamber. In some embodiments, the method further comprises: providing an additional outlet at the bottom of each settling chamber.

The present disclosure also provides a method for converting a vertical HF acid settler to a segmented sulfuric acid settler. The vertical HF acid settler comprises a vertical vessel having an outlet at its top section, a vertical interior wall, a bottom, and internal components comprising an internal baffle extending upwardly from the bottom of the vertical vessel. The method comprises: (a) removing the internal components from the vertical vessel; (b) installing one or more internal vertical walls defining two or more settling chambers within the vessel, said one or more internal vertical walls extending upwardly from the bottom of the vertical vessel; (c) retaining the outlet which is at the top section of the vertical vessel; (d) providing a first coalescing media extending substantially the full diameter of the vertical vessel, the first coalescing media being positioned above the one or more internal vertical walls; and (e) providing an inlet and an outlet for each of said two or more settling chambers, the outlet of a settling chamber being positioned below the inlet of said settling chamber.

In some embodiments, the method further comprises: providing a second coalescing media extending substantially the full diameter of the vertical vessel, the second coalescing media being spaced above the first coalescing media but below the outlet at the top section of the vertical vessel.

In some embodiments, the method further comprises: providing an additional outlet at the bottom of at least one settling chamber. In some embodiments, the method further comprises: providing an additional outlet at the bottom of each settling chamber.

Each settling chamber has a top, a bottom and vertical sides. The bottom and vertical sides are closed, that is, there is no liquid flow in or out of a settling chamber through the bottom or vertical sides except through specified inlets or outlets at the bottom or vertical sides of the settling chamber. Typically, the bottom of a settling chamber is formed by the bottom of the vertical vessel, and the vertical sides of a settling chamber is formed by the vertical interior wall of the vertical vessel and one or more internal vertical walls. The top of settling chamber is open. In some embodiments, the top of each settling chamber is covered by the first coalescing media.

Figure 6:
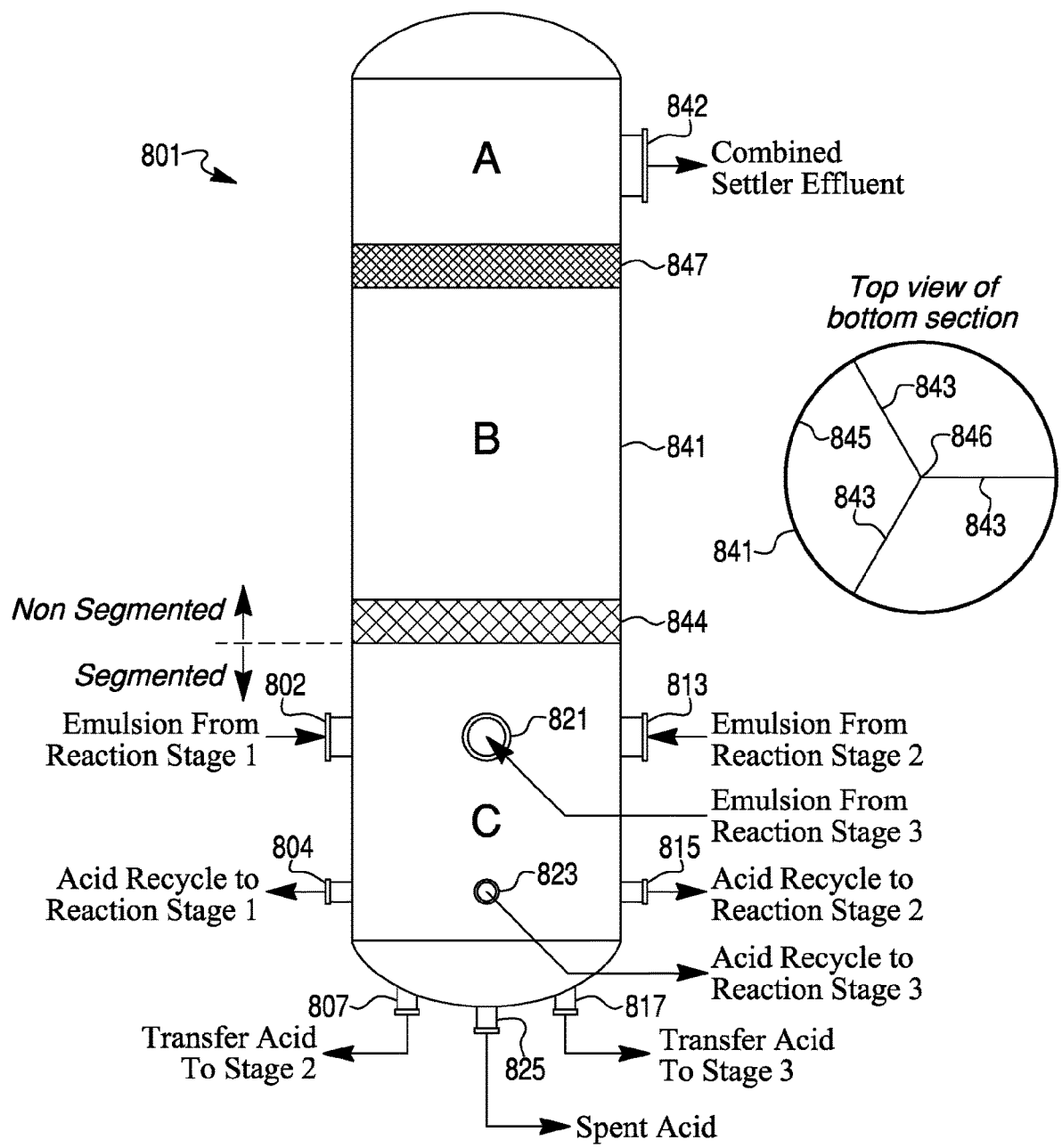
FIG. 6 shows an elevation view and a cross-sectional view of the segmented sulfuric acid settler of FIG. 5.

The first coalescing media and the second coalescing media divide the vertical vessel into three sections: a top section which is above the second coalescing media, a middle section between the first coalescing media and the second coalescing media, and a bottom section which is below the first coalescing media. Only the bottom section is segmented by internal vertical wall(s). The top and middle sections are not segmented (FIG. 6).

In some embodiments, the first coalescing media extends substantially horizontally through the internal space of the vertical vessel. In some embodiments, the second coalescing media also extends substantially horizontally through the internal space of the vertical vessel. In some embodiments, the first coalescing media and the second coalescing media are substantially parallel to each other. In some embodiments, the periphery of the first coalescing media is attached to the interior wall of the vertical vessel. In some embodiments, the periphery of the second coalescing media is attached to the interior wall of the vertical vessel.

In some embodiments, the first coalescing media and/or the second coalescing media may comprise one or more layers of coalescing fiber or coalescing media. In some embodiments, the first coalescing media is a bulk separation coalescing media which acts to keep most SA in the bottom section of the vertical vessel. In some embodiments, the hydrocarbon/SA mixture in the middle section comprises no more than 50 wt %, or 40 wt %, or 30 wt %, or 20 wt %, or 10 wt %, or 5 wt % of SA in the mixture. In some embodiments, the second coalescing media is a fine separation coalescing media which acts to further separate SA phase from hydrocarbon phase. In some embodiments, the hydrocarbon/SA mixture in the top section comprises no more than 500 wppm, or 400 wppm, or 300 wppm, or 200 wppm, or 100 wppm, or 50 wppm, or 15 wppm of SA in the mixture.

In some embodiments, the vertical HF acid settler comprises a vertical vessel having an outlet at its top section or upper end, and such outlet can be retained or modified to provide an outlet at the top section or upper end of the vertical vessel of the sulfuric acid settler.

In some embodiments, the internal baffle in a vertical HF acid settler can be retained or modified to provide at least one internal vertical wall defining settling chambers within the vessel, said internal vertical wall extending upwardly from the bottom of the vertical vessel. In some embodiments, the internal baffle is retained or modified to provide one internal vertical wall defining two settling chambers within the vessel; said one internal vertical wall extending from one side of the vertical interior wall to the other side of the vertical interior wall. In some embodiments, the internal baffle is retained as or modified to become a central vertical wall. By "central vertical wall", it is meant an internal vertical wall substantially passing through the longitudinal axis of the vertical vessel and extending from one side of the vertical interior wall to the opposite side of the vertical interior wall to divide the bottom section of the vessel into two settling chambers with substantially equal volumes.

In some embodiments, additional one or more internal vertical walls defining additional settling chambers within the vertical vessel can be installed, said additional one or more internal vertical walls extending upwardly from the bottom of the vertical vessel and having substantially the same height as the at least one internal vertical wall converted from the internal baffle. In some embodiments, the internal baffle is retained as or converted to a central vertical wall, and two additional internal vertical walls can be installed within the vessel, both are substantially parallel to the central vertical wall. In some embodiments, these three substantially parallel internal vertical walls divide the bottom section of the vessel into four settling chambers with substantially equal volumes.

In some embodiments, the internal baffle is retained as or converted to a central vertical wall, and two additional internal vertical walls can be installed within the vessel: one is substantially perpendicular to the central vertical wall and extends from substantially the vertical axis of the central vertical wall to one side of the vertical interior wall, the other is also substantially perpendicular to the central vertical wall and extends from substantially the vertical axis of the central vertical wall to the other side of the vertical interior wall. Such two additional internal vertical walls are substantially aligned with each other across the center of the vertical vessel. In such embodiments, the vertical walls divide the bottom section of the vertical vessel into four settling chambers with substantially equal volumes.

In some embodiments, the internal baffle in a vertical HF acid settler is removed and decommissioned. In some embodiments, all internal components including the internal baffle within the vertical vessel of the vertical HF acid settler are removed. In such embodiments, one or more new internal vertical walls defining two or more settling chambers within the vertical vessel are installed, said one or more internal vertical walls extending upwardly from the bottom of the vertical vessel. In some embodiments, a central vertical wall is installed to divide the bottom section of the vertical vessel into two settling chambers with substantially equal volumes.

In some embodiments, two substantially parallel internal vertical walls can be installed within the vessel to divide the bottom section of the vessel into three settling chambers. These two substantially parallel internal vertical walls respectively extend upwardly from the bottom of the vertical vessel and extend from one side of the vertical interior wall to the other side of the vertical interior wall. In some embodiments, these three settling chambers have substantially equal volumes.

In some embodiments, a plurality of internal vertical walls can be installed defining a plurality of settling chambers within the vessel. In some embodiments, said plurality of internal vertical walls are substantially parallel to each other. In some embodiments, each internal vertical wall extends substantially radially inwardly from the vertical interior wall of the vertical vessel. In some embodiments, the number of said plurality of internal vertical walls is two, three, or four.

In some embodiments, as shown in FIGS. 5 and 6, three internal vertical walls 843 are installed within the vessel 841, each having an upper end, a lower end, and two vertical side edges. The lower end of each internal vertical wall is sealingly attached to the bottom of the vertical vessel so that liquid cannot flow from one settling chamber to the other across the lower end of the internal vertical wall. In some embodiments, the lower end of each internal vertical wall is sealed by mechanical attachments to the bottom of the vertical vessel. Each internal vertical wall extends upwardly from the bottom of the vertical vessel to the bottom of the first coalescing media. In some embodiments, the upper ends of all the internal vertical walls are at substantially the same elevation. Each internal vertical wall 843 extends substantially radially inwardly from the vertical interior wall 845 of the vertical vessel 841. One vertical side edge of each internal vertical wall is respectively sealingly attached to the vertical interior wall 845 of the vertical vessel. The opposite vertical side edges of the internal vertical walls 843 are sealingly attached to each other at substantially the longitudinal axis 846 of the vertical vessel 841 to form enclosed spaces in between. In such embodiments, said three internal vertical walls divide the bottom section C of the vessel into three settling chambers. In some embodiments, such three settling chambers have substantially equal volumes.

As shown in FIGS. 5 and 6, an inlet 802, 813, 821 and an outlet 804, 815, 823 are provided or installed for each settling chamber. For each settling chamber, the outlet is positioned below the inlet. In some embodiments, an additional outlet 807, 817, 825 can be provided or installed for a settling chamber, said additional outlet also being positioned below the inlet of said settling chamber. In some embodiments, an additional outlet can be provided or installed for each settling chamber. In some embodiments, the additional outlet is provided or installed at the bottom of a settling chamber. In some embodiments, the additional outlet is provided or installed at the bottom of each settling chamber.

The present disclosure provides a segmented sulfuric acid settler for separating a sulfuric acid phase from a hydrocarbon phase. The sulfuric acid settler comprises: (a) a vertical vessel having an outlet at its top section, a vertical interior wall, and a bottom; (b) at least one internal vertical wall defining two or more settling chambers within the vessel; (c) an inlet for each settling chamber for ingress of a sulfuric acid/hydrocarbon emulsion; (d) an outlet for each settling chamber located below the inlet for that settling chamber for exit of the sulfuric acid phase from that settling chamber; and (e) a coalescing media extending substantially the full diameter of the vertical vessel, the coalescing media being positioned above the at least one internal vertical wall. In some embodiments, the vertical vessel is substantially cylindrical. In some embodiments, the at least one internal vertical wall extends upwardly from the bottom of the vertical vessel. In some embodiments, the at least one internal vertical wall extends upwardly from the bottom of the vertical vessel to the coalescing media.

In some embodiments, the coalescing media comprises a first coalescing media and a second coalescing media. In such embodiments, the segmented sulfuric acid settler comprises: (a) a vertical vessel having an outlet at its top section, a vertical interior wall, and a bottom; (b) at least one internal vertical wall defining two or more settling chambers within the vessel; (c) an inlet for each settling chamber for ingress of a sulfuric acid/hydrocarbon emulsion; (d) an outlet for each settling chamber located below the inlet for that settling chamber for exit of the sulfuric acid phase from that settling chamber; (e) a first coalescing media extending substantially the full diameter of the vertical vessel, the first coalescing media being positioned above the at least one internal vertical wall; and (f) a second coalescing media extending substantially the full diameter of the vertical vessel, the second coalescing media being spaced above the first coalescing media but below the outlet at the top section of the vessel. In some embodiments, the at least one internal vertical wall extends upwardly from the bottom of the vertical vessel to the first coalescing media.

In some embodiments, the sulfuric acid settler further comprises an additional outlet for at least one settling chamber. In some embodiments, the sulfuric acid settler further comprises an additional outlet for each settling chamber. The additional outlet is located below the inlet for that settling chamber for exit of the sulfuric acid phase from that settling chamber. In some embodiments, the additional outlet is located at the bottom of the vertical vessel.

The vertical vessel has an outlet at its top section. In some embodiments, the outlet is at the upper end or the top of the vertical vessel. Each settling chamber is defined by corresponding internal vertical wall(s), vertical interior wall of the vertical vessel, and the bottom of the vertical vessel. They form an enclosed space for each settling chamber with an open top. In some embodiments, the internal vertical wall(s) of a settling chamber extends upwardly from the bottom of the vertical vessel to the bottom of the first coalescing media, and the settling chamber is further defined by the first coalescing media. In some embodiments, there are two settling chambers in the segmented sulfuric acid settler. In some embodiments, there are three settling chambers in the segmented sulfuric acid settler. In some embodiments, there are four settling chambers in the segmented sulfuric acid settler.

In some embodiments, each settling chamber has substantially the same volume. In some embodiments, the volume of the settling chambers varies within a range of ±30%, or ±20%, or ±15%, or ±10% by volume, that is, the volume of one settling chamber is no more or no less than the volume of another settling chamber by 30%, or 20%, or 15%, or 10%. The internal vertical wall, vertical interior wall of the vertical vessel, and the bottom of the vertical vessel are all of gas and/or liquid impermeable materials. In some embodiments, the bottom of a settling chamber is closed without an outlet in it. In some embodiments, an outlet can be located in the bottom of a settling chamber or in the bottom of each settling chamber.

Only the bottom section is segmented by internal vertical wall(s). The top and middle sections are not segmented.

Coalescing media are installed at two different heights to provide the first (e.g., bulk) and the second (e.g., fine) separation of sulfuric acid from the hydrocarbons. The first coalescing media and the second coalescing media divide the vertical vessel into three sections: a top section which is above the second coalescing media, a middle section between the first coalescing media and the second coalescing media, and a bottom section which is below the first coalescing media. Combined settler effluent exits from the top section of the vertical vessel. In some embodiments, the settler effluent can be purified and fractionated to produce an alkylate product. In some embodiments, the settler effluent flows through the reactor tube bundles to remove the heat of the alkylation reaction before being purified and fractionated.

There is typically one, two, three, four or five internal vertical wall(s) in a segmented sulfuric acid settler. Each internal vertical wall is of a liquid impermeable material. Each internal vertical wall has an upper end, a lower end, and two vertical side edges. The lower end of each internal vertical wall is sealingly attached to the bottom of the vertical vessel. In some embodiments, at least one internal vertical wall extends upwardly from the bottom of the vertical vessel to the first coalescing media. In some embodiments, at least one internal vertical wall is sealed at its upper end to the first coalescing media. In some embodiments, each internal vertical wall extends upwardly from the bottom of the vertical vessel to the bottom of the first coalescing media. In some embodiments, the upper ends of all the internal vertical walls are at substantially the same elevation, that is, all the internal vertical walls have substantially the same height. In some embodiments, each internal vertical wall is sealed at its upper end to the first coalescing media.

In some embodiments, internal vertical walls are substantially parallel to each other. In such embodiments, the internal vertical walls respectively extend from one side of the vertical interior wall to the other side of the vertical interior wall, and both vertical side edges of each internal vertical wall are respectively sealingly attached to the vertical interior wall of the vertical vessel.

In some embodiments, each internal vertical wall extends substantially radially inwardly from the vertical interior wall of the vertical vessel. In such embodiments, one vertical side edge of each internal vertical wall is respectively sealingly attached to the vertical interior wall of the vertical vessel, the other vertical side edge (opposite vertical side edge) of each internal vertical wall are sealingly attached to each other at substantially the longitudinal axis of the vertical vessel to enclose the spaces between neighboring internal vertical walls to form settling chambers. In some embodiments, the number of the internal vertical walls is three to five, and the internal vertical walls extend substantially radially inwardly from the vertical interior wall of the vertical vessel. In some embodiments, three internal vertical walls respectively extend substantially radially inwardly from the vertical interior wall of the vertical vessel to divide the bottom section of the vessel into three settling chambers with substantially the same volume.

Each settling chamber has an inlet for ingress of a sulfuric acid/hydrocarbon emulsion from a sulfuric acid alkylation reaction zone (stage). Each settling chamber also has an outlet for recycling the sulfuric acid phase from that settling chamber to the sulfuric acid alkylation reaction zone (stage) or for transferring the sulfuric acid phase from that settling chamber to the immediately subsequent sulfuric acid alkylation reaction zone (stage) during an acid staging process. In some embodiments, a settling chamber can have an additional outlet for transferring the sulfuric acid phase from that settling chamber to the immediately subsequent sulfuric acid alkylation reaction zone (stage) during an acid staging process. In some embodiments, each settling chamber can have an additional outlet, and the additional outlet of the final settling chamber is used to send spent acid to be purged to the sulfuric acid blowdown section of the converted SA alkylation unit. For each settling chamber, the outlet and the additional outlet are positioned below the inlet. In some embodiments, the additional outlet is at the bottom of a settling chamber.

FIGS. 5 and 6 depict an embodiment of the segmented sulfuric acid settler. The segmented sulfuric acid settler 801 comprises a substantially cylindrical vertical vessel 841 having an outlet 842 at its top section A. There are three internal vertical walls 843 respectively extending upwardly from the bottom of the vertical vessel to the bottom of the first coalescing media 844. The first coalescing media 844 is a bulk separation coalescing media. Each internal vertical wall 843 extends substantially radially inwardly from the vertical interior wall 845 of the vertical vessel 841. One vertical side edge of each internal vertical wall 843 is respectively sealingly attached to the vertical interior wall 845 of the vertical vessel 841, the other vertical side edge (opposite vertical side edge) of each internal vertical wall 843 are sealingly attached to each other at substantially the longitudinal axis 846 of the vertical vessel 841 to enclose the spaces between neighboring internal vertical walls to form three settling chambers with substantially equal volume.

The first coalescing media 844 and the second coalescing media 847 divide the vertical vessel 841 into three sections: a top section A which is above the second coalescing media 847, a middle section B between the first coalescing media 844 and the second coalescing media 847, and a bottom section C which is below the first coalescing media 844. The second coalescing media 847 is a fine separation coalescing media. Only the bottom section C is segmented by internal vertical walls 843.

The first settling chamber has an inlet 802, an outlet 804 and an additional outlet 807. The second settling chamber has an inlet 813, an outlet 815 and an additional outlet 817. The third settling chamber has an inlet 821, an outlet 823 and an additional outlet 825. The outlet and the additional outlet of each settling chamber are located below the inlet for that settling chamber. Outlet 804 and additional outlet 807 are located below inlet 802. Outlet 815 and additional outlet 817 are located below inlet 813. Outlet 823 and additional outlet 825 are located below inlet 821.

The present disclosure also provides a method for converting an HF alkylation unit which utilizes HF as a reaction catalyst to a SA alkylation unit. The method comprises: (a) substituting sulfuric acid for hydrogen fluoride as the reaction catalyst; and (b) modifying a suitable vessel in the hydrogen fluoride alkylation unit to provide a segmented sulfuric acid settler as disclosed in this disclosure. In some embodiments, the suitable vessel is a vertical HF acid settler in the HF alkylation unit, and said vertical HF acid settler is modified to provide a segmented sulfuric acid settler.

The present disclosure also provides a method for converting an HF alkylation unit which utilizes HF as a reaction catalyst to a SA alkylation unit. The method comprises: (a) substituting sulfuric acid for hydrogen fluoride as the reaction catalyst; and (b) providing a new segmented sulfuric acid settler as disclosed in this disclosure. In some embodiments, the vertical HF acid settler is decommissioned.

In some embodiments, the above HF alkylation unit conversion methods (either when a suitable vessel is modified to provide a segmented SA settler or when a new segmented SA settler is provided) further comprise: (c) providing two or more sulfuric acid alkylation reaction zones disposed in sequence, each sulfuric acid alkylation reaction zone having a sulfuric acid/hydrocarbon emulsion outlet and a sulfuric acid inlet, the number of the sulfuric acid alkylation reaction zones and the number of the settling chambers being equal; and (d) providing conduits connecting the sulfuric acid/hydrocarbon emulsion outlet and the sulfuric acid inlet of a sulfuric acid alkylation reaction zone with the inlet and the outlet of a settling chamber respectively so that each sulfuric acid alkylation reaction zone is connected or coupled with a different settling chamber to form one-to-one correspondence.

By "sulfuric acid/hydrocarbon emulsion outlet (of a sulfuric acid alkylation reaction zone (stage))", it is meant a reactor outlet, a pump or other device, or a conduit for egress of the sulfuric acid/hydrocarbon emulsion from the sulfuric acid alkylation reaction zone (stage). By "sulfuric acid inlet (of a sulfuric acid alkylation reaction zone (stage))", it is meant a reactor inlet, a pump or other device, or a conduit for receiving or recycling sulfuric acid into the sulfuric acid alkylation reaction zone (stage).

In some embodiments, the converted SA alkylation unit comprising a segmented sulfuric acid settler enables an acid staging process which can reduce acid consumption and improve alkylate quality by staging the SA flow through the unit. In such embodiments, the HF alkylation unit conversion method further comprises: providing a conduit connecting the sulfuric acid inlet of a non-first sulfuric acid alkylation reaction zone (stage) with an outlet or an additional outlet (if present) of the immediately preceding settling chamber. In some embodiments, the HF alkylation unit conversion method further comprises: providing conduits connecting the sulfuric acid inlet of each non-first sulfuric acid alkylation reaction zone (stage) with an outlet or an additional outlet (if present) of the immediately preceding settling chamber.

In this disclosure, the terms "(sulfuric acid alkylation) reaction zone" and "(sulfuric acid alkylation) reaction stage" can be used interchangeably. Each sulfuric acid alkylation reaction zone (stage) can independently comprise one or more sulfuric acid alkylation reactors. In some embodiments, each sulfuric acid alkylation reaction zone (stage) is a sulfuric acid alkylation reactor. In some embodiments, each sulfuric acid alkylation reaction zone (stage) comprises two sulfuric acid alkylation reactors. In some embodiments, each sulfuric acid alkylation reaction zone (stage) independently comprises one or two sulfuric acid alkylation reactors. In some embodiments, a sulfuric acid alkylation reaction zone (stage) comprises an alkylation reactor vessel and its affiliated device(s) such as static mixer, rotor stator mixer and/or emulsion recycle pump.

When a sulfuric acid alkylation reaction zone (stage) comprises two or more sulfuric acid alkylation reactors, each sulfuric acid alkylation reactor can have a sulfuric acid/hydrocarbon emulsion outlet and a sulfuric acid inlet. In such embodiments, the term "sulfuric acid/hydrocarbon emulsion outlet of a sulfuric acid alkylation reaction zone (stage)", as used herein, means the sulfuric acid/hydrocarbon emulsion outlet of each sulfuric acid alkylation reactor in such sulfuric acid alkylation reaction zone (stage) collectively. Similarly, the term "sulfuric acid inlet of a sulfuric acid alkylation reaction zone (stage)", as used herein, means the sulfuric acid inlet of each sulfuric acid alkylation reactor in such sulfuric acid alkylation reaction zone (stage) collectively. Multiple sulfuric acid/hydrocarbon emulsion outlets in a sulfuric acid alkylation reaction zone (stage) can jointly or independently connect with the inlet of the corresponding settling chamber. Similarly, multiple sulfuric acid inlets in a sulfuric acid alkylation reaction zone (stage) can jointly or independently connect with the outlet or the additional outlet of the corresponding settling chamber.

Figure 15:
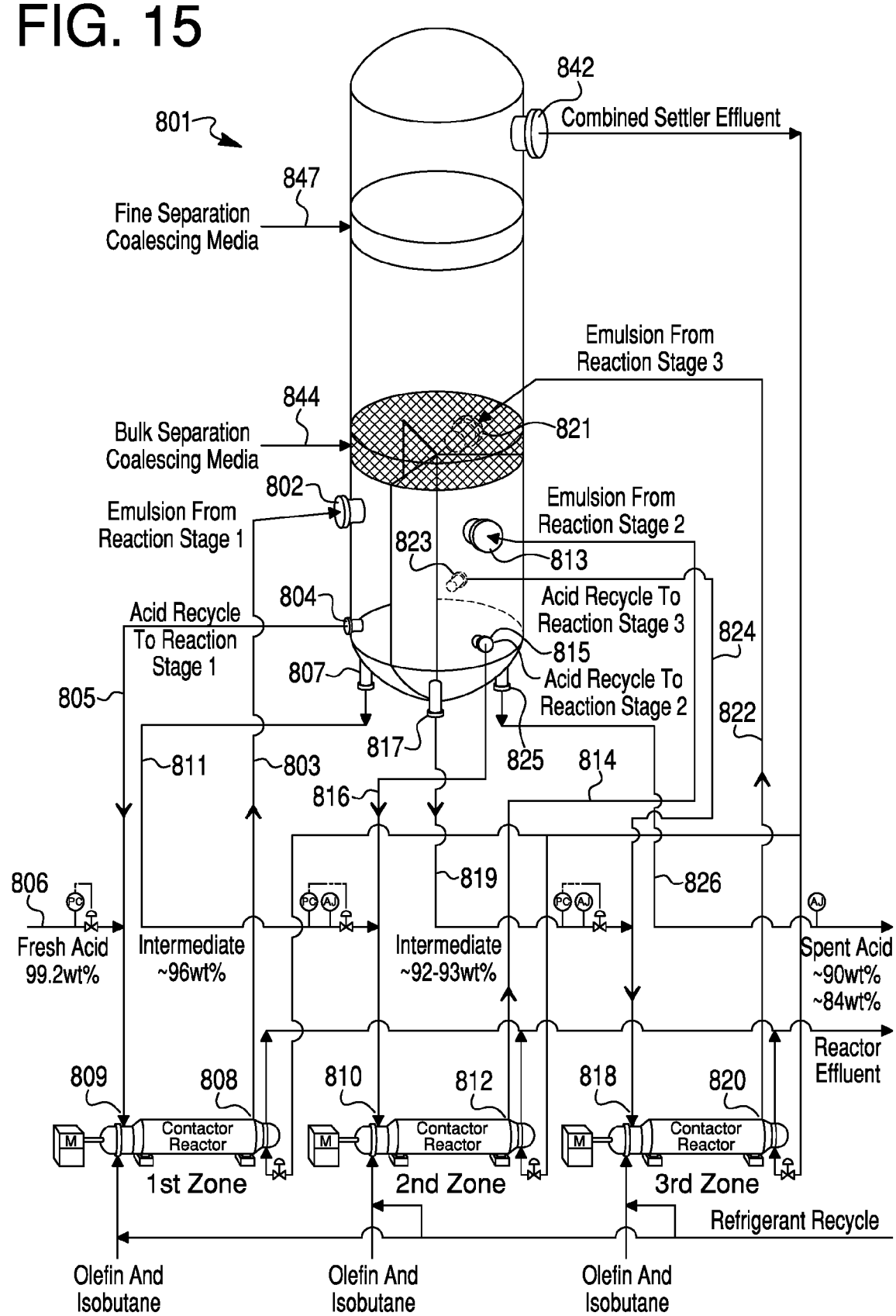
FIG. 15 shows a converted SA alkylation unit design integrated with the sulfuric acid staging concepts.

In some embodiments, as shown in FIGS. 5, 6 and 15, the converted SA alkylation unit comprises three sulfuric acid alkylation reaction zones (stages) disposed in sequence and a segmented sulfuric acid settler 801 having three settling chambers. Each sulfuric acid alkylation reaction zone (stage) has a sulfuric acid/hydrocarbon emulsion outlet and a sulfuric acid inlet, and each settling chamber has an outlet, an inlet, and an additional outlet. In some embodiments, one or more settling chambers may have no additional outlet.

The sulfuric acid/hydrocarbon emulsion outlet 808 of a first sulfuric acid alkylation reaction zone (first zone) is connected with the inlet 802 of a first settling chamber so that the sulfuric acid/hydrocarbon emulsion 803 from the first zone flows into the first settling chamber. The outlet 804 of the first settling chamber is connected with the sulfuric acid inlet 809 of the first zone so that a portion of the sulfuric acid phase 805 separated out in the first settling chamber can be recycled to the first zone. In some embodiments, a fresh sulfuric acid 806 having acid strength of 99.2 wt % can be added to the sulfuric acid recycle stream 805 to the first zone. The additional outlet 807 of the first settling chamber is connected with the sulfuric acid inlet 810 of a second sulfuric acid alkylation reaction zone (second zone) so that a portion of the sulfuric acid phase 811 having acid strength of about 96 wt % separated out in the first settling chamber can be fed to the second zone.

In some embodiments, the outlet 804 or the additional outlet 807 (if present) of the first settling chamber can be connected with the sulfuric acid inlet 810 of a second sulfuric acid alkylation reaction zone (second zone) so that a portion of the sulfuric acid phase 805 or 811 separated out in the first settling chamber can be fed to the second zone.

The sulfuric acid/hydrocarbon emulsion outlet 812 of the second zone is connected with the inlet 813 of a second settling chamber so that the sulfuric acid/hydrocarbon emulsion 814 from the second zone flows into the second settling chamber. The outlet 815 of the second settling chamber is connected with the sulfuric acid inlet 810 of the second zone so that a portion of the sulfuric acid phase 816 in the second settling chamber can be recycled to the second zone. In some embodiments, a fresh sulfuric acid can be added to the sulfuric acid recycle stream 816 to the second zone. In some embodiments, the outlet 815 or the additional outlet 817 of the second settling chamber can be connected with the sulfuric acid inlet 818 of a third sulfuric acid alkylation reaction zone (third zone) so that a portion of the sulfuric acid phase 816 or 819 having acid strength of about 92 to 93 wt % in the second settling chamber can be fed to the third zone.

The sulfuric acid/hydrocarbon emulsion outlet 820 of the third zone is connected with the inlet 821 of the third settling chamber so that the sulfuric acid/hydrocarbon emulsion 822 from the third zone flows into the third settling chamber. The outlet 823 of the third settling chamber is connected with the sulfuric acid inlet 818 of the third zone so that a portion of the sulfuric acid phase 824 in the third settling chamber can be recycled to the third zone. In some embodiments, no fresh sulfuric acid is added to the third zone. A portion of the sulfuric acid phase in the third settling chamber exits the outlet 823 or the additional outlet 825 of the third settling chamber as spent acid 826 having acid strength of about 84 wt % or about 90 wt % and can be sent to the sulfuric acid blowdown section of the converted SA alkylation unit to be purged. In some embodiments, fresh sulfuric acid can be added to all non-final sulfuric acid alkylation reaction zones (stages).

The present disclosure further provides a converted SA alkylation unit comprising a segmented sulfuric acid settler as disclosed in this disclosure. In some embodiments, the converted SA alkylation unit further comprises two or more SA alkylation reaction zones disposed in sequence, wherein the number of the SA alkylation reaction zones and the number of the settling chambers are equal. In some embodiments, each SA alkylation reaction zone has a sulfuric acid/hydrocarbon emulsion outlet and a sulfuric acid inlet, the emulsion outlet and the sulfuric acid inlet of each sulfuric acid alkylation reaction zone is fluidly connected with the inlet and the outlet of a different settling chamber respectively. In some embodiments, the sulfuric acid inlet of a non-first sulfuric acid alkylation reaction zone is fluidly connected with an outlet or an additional outlet (if present) of the immediately preceding settling chamber. In some embodiments, the sulfuric acid inlet of each non-first sulfuric acid alkylation reaction zone is fluidly connected with an outlet or an additional outlet (if present) of the immediately preceding settling chamber. In some embodiments, the present disclosure further provides an alkylation process comprising contacting an olefin with an isoparaffin in the presence of a sulfuric acid catalyst to produce a product mixture comprising an alkylate wherein the contacting is performed in the two or more sulfuric acid alkylation reaction zones disposed in sequence and connected or coupled with settling chambers to form one-to-one correspondence.

The present disclosure further provides an alkylation process performed in a converted SA alkylation unit as disclosed in this disclosure. The alkylation process comprises contacting an olefin with an isoparaffin in the presence of a sulfuric acid catalyst to produce a product mixture comprising an alkylate wherein the contacting is performed in a SA alkylation reactor or a SA alkylation reaction zone in the converted SA alkylation unit.

Alkylation reactions of this disclosure are carried out with molar ratio of isoparaffin to olefin introduced into the SA alkylation reactor or the SA alkylation reaction zone of greater than 1 to minimize undesired polymerization reactions. The term "molar ratio of isoparaffin to olefin introduced into the SA alkylation reactor or the SA alkylation reaction zone", as used herein, means the molar ratio of the total amount of isoparaffin to the total amount of olefin introduced into the SA alkylation reactor or the SA alkylation reaction zone. In some embodiments, the molar ratio of isoparaffin to olefin introduced into the SA alkylation reactor or the SA alkylation reaction zone is in the range of from about 2:1 to about 50:1, or in the range of from about 4:1 to about 20:1, or in the range of from about 5:1 to about 12:1.

The sulfuric acid catalyst in this disclosure comprises a sulfuric acid. Typically, the sulfuric acid catalyst in this disclosure comprises, consists essentially of, or consists of an aqueous solution of sulfuric acid. The acid strength of the sulfuric acid solution in the SA alkylation reactor or the SA alkylation reaction zone is generally maintained high enough to avoid dilution of the acid catalyst and excessive side reactions, but low enough to avoid high viscosity acid (freezing acid). In some embodiments, the acid strength of the sulfuric acid solution in the SA alkylation reactor or the SA alkylation reaction zone is in the range of about 80 wt % to about 99.5 wt %, or in the range of about 86 wt % to about 99 wt %.

The volume ratio of the sulfuric acid solution to the total amount of olefin and isoparaffin in the SA alkylation reactor or the SA alkylation reaction zone can be in the range of from about 0.5:1 to about 2.5:1, or from about 0.7:1 to about 2.3:1, or from about 0.8:1 to about 2.0:1, or from about 0.9:1 to about 1.8:1, or from about 1:1 to about 1.5:1, or from about 1:1 to about 1.2:1.

The alkylation reactions can be carried out at effective conditions in the reactor to generate a product mixture comprising alkylate. For example, the temperature in the SA alkylation reactor or the SA alkylation reaction zone can be in the range of from about 0° C. to about 30° C. In some embodiments, the temperature in the SA alkylation reactor or the SA alkylation reaction zone is in the range of from about 4° C. to about 20° C. In some embodiments, the temperature in the SA alkylation reactor or the SA alkylation reaction zone is in the range of from about 7° C. to about 12° C. The pressure in the SA alkylation reactor or the SA alkylation reaction zone can be in the range of from about 1 to about 100 psig, or in the range of from about 30 to about 80 psig, or in the range of from about 40 to about 70 psig.

Many aspects and embodiments have been described above and are merely exemplary and not limiting. After reading this specification, skilled artisans appreciate that other aspects and embodiments are possible without departing from the scope of the invention.

EXAMPLES

The concepts described herein will be further described in the following examples, which do not limit the scope of the invention described in the claims.

Example 1

Example 1 converted an HF alkylation unit which utilizes HF as a reaction catalyst to a SA alkylation unit. The original HF alkylation unit was a gravity-flow HF alkylation unit with a single vertical HF acid settler (Acid Settler in FIG. 16) and four acid coolers (only two were shown in FIG. 16). (Refer to FIG. 16 for a simplified process flow diagram of the original HF alkylation unit.) The fractionation equipment for this particular HF alkylation unit included an Isostripper column and a Depropanizer column. Effluent from the HF acid settler was split into a reflux stream 901 to the Isostripper and a feed stream 902 to the Depropanizer. The Depropanizer overhead product 903 was propane, and the bottom product 904 provided feed to the Isostripper. The Depropanizer also generated a side stream 905 which provided approximately 20% of the recycle isobutane to the reaction section. The isobutane-rich Isostripper overhead stream 906 was condensed and sub-cooled then pumped to the reaction section to provide the remaining 80% of the recycle isobutane. A side stream from the Isostripper was the n-butane product stream, and the bottoms stream was the alkylate product. The design capacity for this unit was 13,500 bpsd (Barrel Per Stream Day) of alkylate product with a feed stream comprising mixed C3's and MTBE (methyl tertiary butyl ether) raffinate.

Figure 17:
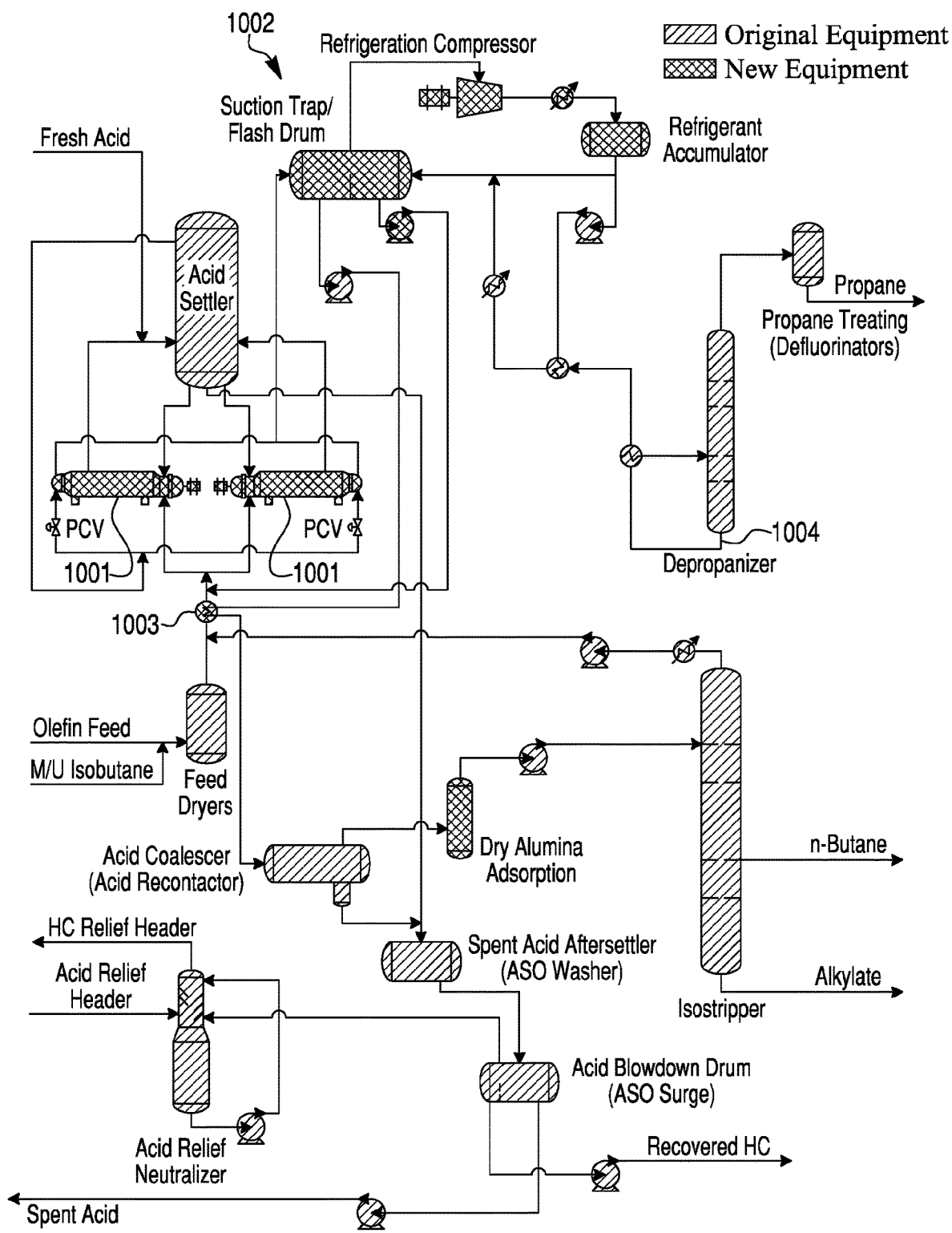
FIG. 17 shows a simplified process flow diagram of the converted SA alkylation unit which is converted from the original HF alkylation unit shown in FIG. 16.

FIG. 17 illustrates a simplified process flow diagram of the conversion solution for this HF alkylation unit; however, olefin feed segregation and sulfuric acid staging are not depicted on this drawing. The conversion methods of this Example involved adding four SA alkylation reactors 1001

(DuPont's STRATCO® Model 74 Contactor™ reactors, two of them were not shown), a refrigeration section 1002 and a feed/effluent heat exchanger 1003, while retaining or repurposing existing equipment to be used for the acid coalescer, propane product treatment and acid blowdown drum. Table 1 provides a list of retained and new major equipment in the SA alkylation unit. As will be appreciated by those skilled in the art, when referring to an equipment or vessel in an HF alkylation unit, or describing an HF alkylation process or an HF alkylation unit, the terms "HF", "HF acid" and "acid" can be used interchangeably. When referring to an equipment or vessel in a SA alkylation unit, or describing a SA alkylation process or a SA alkylation unit, the terms "sulfuric acid" and "acid" can be used interchangeably. Most modern HF alkylation units also have remote HF storage tanks and remote HF acid blowdown drums. Depending on the location of these vessels and the requirements of the conversion solution offered, these may be retained as spent acid aftersettlers, acid blowdown drums, suction trap/flash drums or supplemental SA acid settlers. Potential opportunities to retain or reuse these vessels will be determined on a case-by-case basis. To maximize product quality and minimize acid consumption, the SA alkylation process utilizing the converted SA alkylation unit can be designed to segregate olefin feed and to stage acid flows between reaction zones.

In this Example, the depropanizer tower bottom stream 1004 was rerouted from the isostripper feed to the refrigeration section, which provided recycled refrigerant to the new reaction section, as well as approximately 50% of the isobutane required for the process. Because the Isostripper was designed in the HF alkylation unit to provide 80% of the recycled isobutane requirement, a significant capacity increase was achieved by retaining the existing Isostripper and its associated equipment such as Isostripper charge pump, Isostripper condenser, Isostripper overhead pump and Isostripper reboiler. By optimizing the isobutane-to-olefin ratio and maximizing existing equipment capacity, the capacity could be increased by nearly 70% while similar product quality was maintained. Table 2 provides a summary of feed and product streams for the conversion methods of this Example. Table 3 provides a summary of alkylate properties.

TABLE 2

| | Feed and Product Streams | | | | |
|---|---|---|---|---|---|
| | Olefin Feed | Isobutane Feed | Propane Product | n-Butane Product | Alkylate Product |
| Volume Flow (bpsd) | 17,727 | 14,343 | 3,634 | 473 | 22,601 |

TABLE 1

Major Equipment List

| Existing Equipment Retained or Repurposed | New Equipment Added for Conversion | Existing Equipment Decommissioned |
|---|---|---|
| Acid Blowdown Drum (Remote) | SA Alkylation Reactors | HF Acid Coolers |
| Acid Neutralization Pit | Dry Alumina Adsorption Vessel | HF Acid Rerun |
| Acid Recontactor | Feed/Effluent Heat Exchangers | ASO Heater |
| Acid Relief Neutralizer | Isostripper Accumulator | ASO Pumps |
| Acid Relief Neutralizer Circulation Pump | Refrigerant Accumulator Vessel | Propane KOH Treater |
| Acid Settler | Refrigerant Condensers | Propane Stripper |
| Acid Storage tank (Remote) | Refrigerant Recycle Pumps | HF Acid Regenerator IC4 Superheater |
| Alkylate Cooler | Refrigerant Compressor | |
| ASO Surge Drum | Suction Trap/Flash Drum Separation Vessel | |
| ASO Surge Drum Circulation Pump | | |
| ASO Washer | | |
| ASO Washer Circulation Pumps | | |
| Depropanizer | | |
| Depropanizer Accumulator | | |
| Depropanizer Charge Pumps | | |
| Depropanizer Condensers | | |
| Depropanizer Feed/Bottoms Heat Exchanger | | |
| Depropanizer Feed/Recycle IC4 Heat Exchanger | | |
| Depropanizer Reboiler | | |
| Depropanizer Reflux Pumps | | |
| Depropanizer Side Stream Cooler | | |
| Feed Dryers | | |
| Isostripper | | |
| Isostripper Charge Pumps | | |
| Isostripper Condensers | | |
| Isostripper Overhead Pumps | | |
| Isostripper Reboiler | | |
| Normal Butane Condensers | | |
| Propane Condensers | | |
| Propane Defluorinators | | |

TABLE 2-continued

Feed and Product Streams

| | Olefin Feed | Isobutane Feed | Propane Product | n-Butane Product | Alkylate Product |
|---|---|---|---|---|---|
| Composition (vol %) | | | | | |
| Ethane | 0.09 | 0.00 | 0.43 | 0.00 | 0.00 |
| Propane | 13.19 | 8.53 | 98.00 | 0.00 | 0.00 |
| i-Butane | 9.04 | 87.63 | 1.57 | 2.50 | 0.03 |
| n-Butane | 5.04 | 3.85 | 0.00 | 92.59 | 4.46 |
| 1,3-Butadiene | 0.00 | 0.00 | 0.00 | 0.00 | 0.00 |
| Propylene | 31.35 | 0.00 | 0.00 | 0.00 | 0.00 |
| Butylenes | 39.85 | 0.00 | 0.00 | 0.00 | 0.00 |
| Amylenes | 0.97 | 0.00 | 0.00 | 0.00 | 0.00 |
| C5+ | 0.47 | 0.00 | 0.00 | 4.91 | 95.52 |

TABLE 3

Alkylate Properties

| | |
|---|---|
| % Propylene/Total Olefins (Feed) | 43.4 |
| % Isobutylene/Total Butylenes (Feed) | 0.5 |
| RON | 95.0 |
| (R + M)/2 | 93.5 |
| D-86 T90, ° F. (° C.) | <255 (124) |
| D-86 EP, ° F. (° C.) | <380 (193) |
| Acid Consumption, lb/gal | 0.45-0.50 |
| Alkylate RVP, psi | 6.0 |
| Alkylate Sulfur, ppm | <2 |

Example 2

Figure 18:
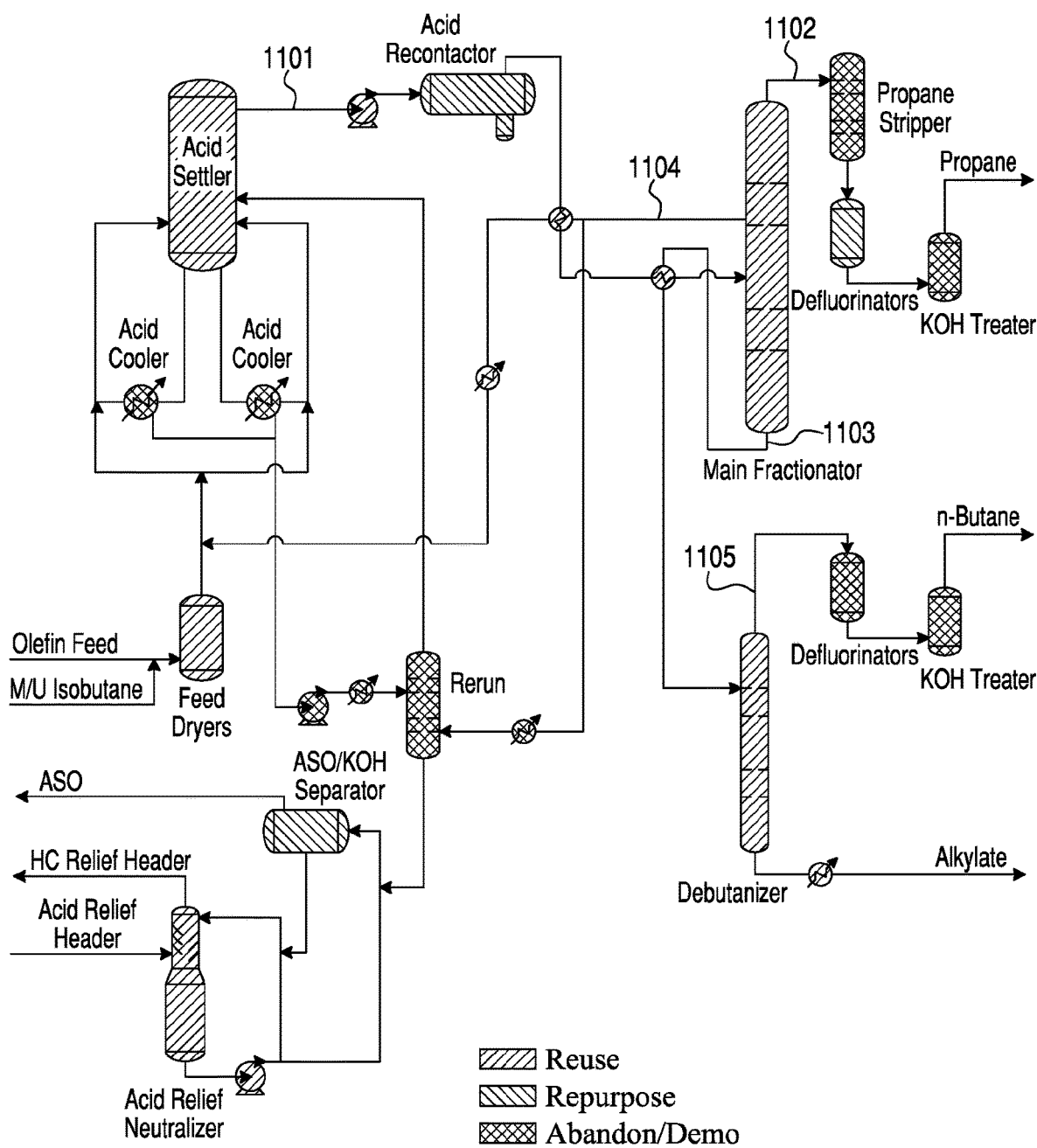
FIG. 18 shows a simplified process flow diagram of an original HF alkylation unit which uses HF as the reaction catalyst to produce alkylate.

Example 2 converted an HF alkylation unit which utilizes HF as a reaction catalyst to a SA alkylation unit. The original HF alkylation unit was a gravity-flow HF alkylation unit with a single vertical HF acid settler (Acid Settler in FIG. 18) and four acid coolers (only two were shown in FIG. 18). (Refer to FIG. 18 for a simplified process flow diagram of the original HF alkylation unit.) The fractionation equipment for this HF alkylation unit included a Main Fractionator column and a Debutanizer column. Effluent 1101 from the HF acid settler provided feed to the Main Fractionator. The Main Fractionator overhead product 1102 was the propane product and the bottoms product stream 1103 provided feed to the Debutanizer. The Main Fractionator also generated a side stream 1104 which provided 100% of the recycle isobutane to the reaction section. The Debutanizer overhead stream 1105 was the n-butane product stream and the Debutanizer bottoms stream was the alkylate product. The design capacity for this unit was 10,000 bpsd (Barrel Per Stream Day) of alkylate product with a feed stream comprising mixed C3's and FCC mixed C4's.

Figure 19:
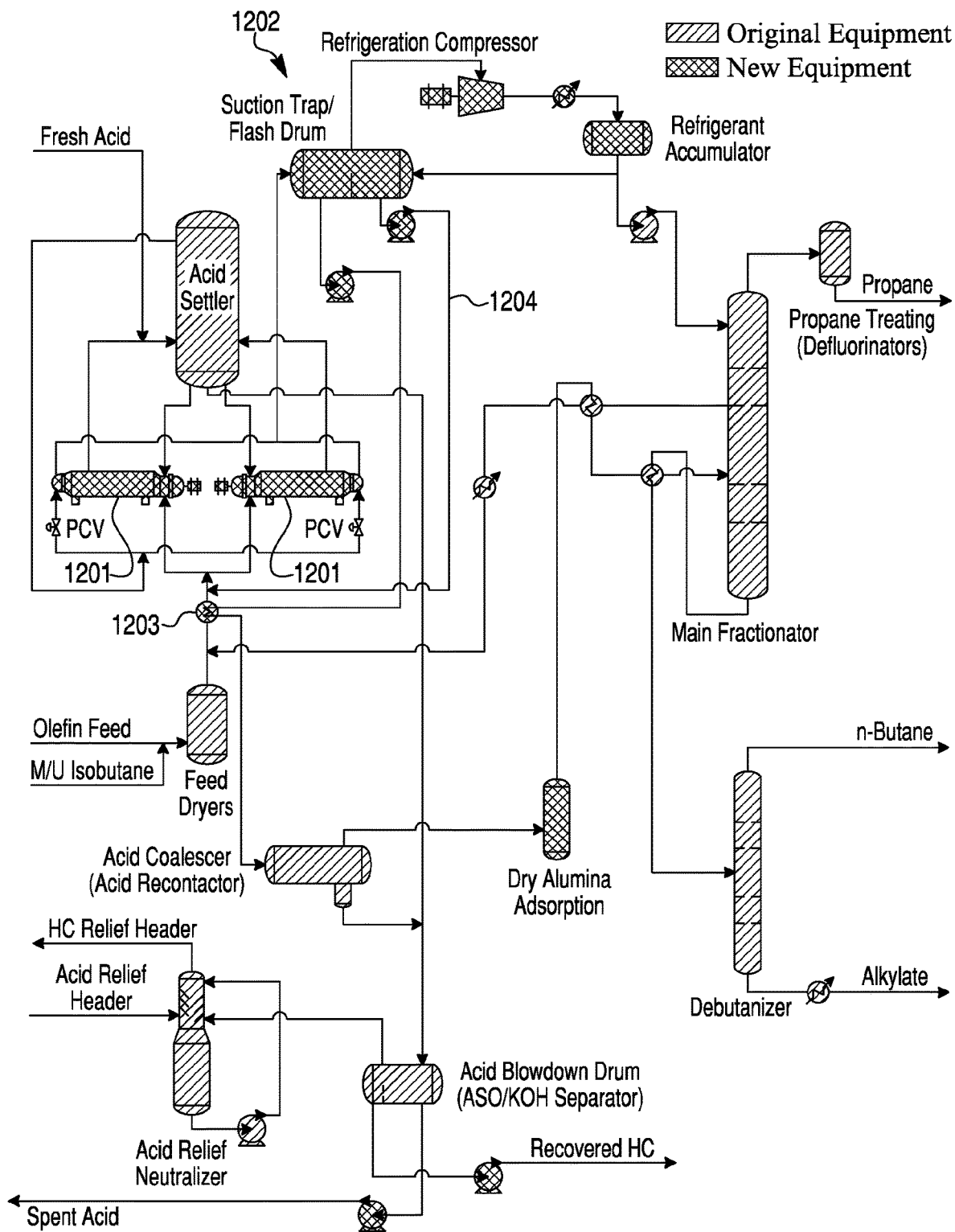
FIG. 19 shows a simplified process flow diagram of the converted SA alkylation unit which is converted from the original HF alkylation unit shown in FIG. 18.

FIG. 19 illustrates a simplified process flow diagram of the conversion solution for this HF alkylation unit; however, olefin feed segregation and sulfuric acid staging are not depicted on this drawing. The conversion methods of this Example involved adding six SA alkylation reactors 1201 (DuPont's STRATCO® Model 74 Contactor™ reactors, four of them were not shown), a refrigeration section 1202, a feed/effluent heat exchanger 1203 and dry alumina adsorption vessel, while retaining or repurposing existing equipment to be used for the acid coalescer, propane product treatment and acid blowdown drum. Table 4 provides a list of retained and new major equipment in the SA alkylation unit. As described in Example 1, most modern HF alkylation units also have remote HF storage tanks and remote HF acid blowdown drums. Depending on the location of these vessels and the requirements of the conversion solution offered, these may be retained as spent acid aftersettlers, acid blowdown drums, suction trap/flash drums or supplemental SA acid settlers. Potential opportunities to retain or reuse these vessels will be determined on a case-by-case basis. To maximize product quality and minimize acid consumption, the SA alkylation process utilizing the converted SA alkylation unit can be designed to segregate olefin feed and to stage acid flows between reaction zones.

TABLE 4

Major Equipment List

| Existing Equipment Retained or Repurposed | New Equipment Added for Conversion | Existing Equipment Decommissioned |
|---|---|---|
| Acid Blowdown Drum (Remote) | SA Alkylation Reactors | HF Acid Coolers |
| Acid Neutralization Pit | Dry Alumina Adsorption Vessel | Acid Rerun |
| Acid Recontactor | Feed/Effluent Heat Exchangers | ASO Heater |
| Acid Relief Neutralizer | Net Effluent Pumps | ASO Pumps |
| Acid Relief Neutralizer Circulation Pump | Recovered Hydrocarbon Pump | n-Butane Defluorinators |
| Acid Settler | Refrigerant Accumulator Vessel | n-Butane KOH Treater |
| Acid Storage tank (Remote) | Refrigerant Condensers | Propane KOH Treater |
| Alkylate Cooler | Refrigerant Recycle Pumps | Propane Stripper |
| ASO/KOH Separator | Refrigerant Compressor | HF Acid Regenerator IC4 Superheater |
| Debutanizer | Spent Acid Pump | |
| Debutanizer Accumulator | Suction Trap/Flash Drum Separation Vessel | |
| Debutanizer Reboiler | | |
| Debutanizer Reflux Pumps | | |
| Feed Dryers | | |
| Main Fractionator | | |
| Main Fractionator Accumulator | | |
| Main Fractionator Condensers | | |
| Main Fractionator Feed Pumps | | |

TABLE 4-continued

Major Equipment List

| Existing Equipment Retained or Repurposed | New Equipment Added for Conversion | Existing Equipment Decommissioned |
|---|---|---|
| Main Fractionator Feed/Bottoms Heat Exchanger | | |
| Main Fractionator Feed/Recycle IC4 Heat Exchanger | | |
| Main Fractionator Reboiler | | |
| Main Fractionator Reflux Pumps | | |
| Main Fractionator Side Stream Cooler | | |
| Normal Butane Condensers | | |
| Propane Condensers | | |
| Propane Defluorinators | | |

In this Example, the converted SA alkylation unit allowed for approximately 50% of the isobutane recycle to be provided by the refrigerant recycle stream 1204 from the new refrigerant section. Because the Main Fractionator was initially designed to provide 100% of the recycled isobutane requirement, a significant capacity increase was achieved by retaining the existing Main Fractionator and its associated equipment such as main fractionator accumulator, main fractionator condenser, main fractionator feed pump, main fractionator feed/bottom heat exchanger, main fractionator feed/recycle isobutane heat exchanger, main fractionator reboiler, main fractionator reflux pump and main fractionator side stream cooler. By optimizing the isobutane-to-olefin ratio and maximizing existing equipment capacity, the capacity could be increased by over 175% while similar product quality was maintained. Table 5 provides a summary of feed and product streams for the conversion solution offered for Example 2. Table 6 provides a summary of alkylate properties. Table 7 provides examples of capacity expansion including Examples 1 and 2 disclosed above. HF unit means the existing HF alkylation unit, and SA unit means the converted SA alkylation unit.

TABLE 5

Feed and Product Streams

| | Olefin Feed | Isobutane Feed | Propane Product | n-Butane Product | Alkylate Product |
|---|---|---|---|---|---|
| Volume Flow (bpsd) | 25,190 | 13,150 | 3,458 | 139 | 27,810 |
| Composition (vol %) | | | | | |
| Ethane | 0.03 | 0.00 | 0.24 | 0.00 | 0.00 |
| Propane | 11.01 | 1.99 | 97.50 | 0.00 | 0.00 |
| i-Butane | 19.51 | 95.00 | 2.24 | 17.09 | 0.76 |
| n-Butane | 6.25 | 3.01 | 0.02 | 81.91 | 6.67 |
| 1,3-Butadiene | 0.06 | 0.00 | 0.00 | 0.00 | 0.00 |
| Propylene | 29.91 | 0.00 | 0.00 | 0.00 | 0.00 |
| Butylenes | 29.62 | 0.00 | 0.00 | 0.00 | 0.00 |
| Amylenes | 0.64 | 0.00 | 0.00 | 0.00 | 0.00 |
| C5+ | 2.98 | 0.00 | 0.00 | 1.00 | 92.57 |

TABLE 6

Alkylate Properties

| | |
|---|---|
| % Propylene/Total Olefins (Feed) | 49.7 |
| % Isobutylene/Total Butylenes | 32.5 |
| (Feed) | |
| RON | 93.0 |
| (R + M)/2 | 92.0 |
| D-86 T90, °F. (°C.) | <275 (135) |
| D-86 EP, °F. (°C.) | <400 (204) |
| Acid Consumption, lb/gal | 0.50-0.55 |
| Alkylate RVP, psi | 6.0 |
| Alkylate Sulfur, ppm | <2 |

TABLE 7

Capacity Expansion

| Example | Feed Type | HF Unit Capacity (bpsd) | SA Unit Capacity (bpsd) | Capacity Increase |
|---|---|---|---|---|
| 1 | MTBE $C_3^=/C_4^=$ | 13,500 | 22,600 | +68% |
| 2 | FCC $C_3^=/C_4^=$ | 10,000 | 27,810 | +178% |
| 3 | MTBE $C_4^=$ | 13,500 | 24,435 | +81% |
| 4 | FCC $C_3^=/C_4^=$ | 10,500 | 20,569 | +96% |
| 5 | FCC $C_4^=$ | 20,500 | 43,865 | +114% |
| 6 | FCC $C_3^=/C_4^=$ | 10,000 | 24,309 | +143% |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination.

EMBODIMENTS

For further illustration, additional non-limiting embodiments of the present disclosure are set forth below.

For example, embodiment 1 is a method for converting a hydrogen fluoride alkylation unit which utilizes hydrogen fluoride as a reaction catalyst to a sulfuric acid alkylation unit. The hydrogen fluoride alkylation unit comprises an HF alkylation reactor, an HF alkylation fractionation section comprising at least one fractionator, and an HF acid relief neutralizer vessel. The method comprises: (a) substituting sulfuric acid for hydrogen fluoride as the reaction catalyst; (b) retaining the HF acid relief neutralizer vessel as a blowdown vapor scrubber; (c) retaining the HF alkylation fractionation section as a sulfuric acid alkylation fractionation section; (d) providing at least one sulfuric acid alkylation reactor; (e) providing a refrigeration section comprising a refrigerant compressor and a heat exchanger for condensing a vapor stream from the refrigerant compressor; (f) providing a conduit for recycling an isoparaffin comprising isobutane from the refrigeration section to said at least one sulfuric acid alkylation reactor; and (g) providing a feed/effluent heat exchanger for cooling a hydrocarbon feed stream and heating a net effluent stream.

Embodiment 2 is a method as set forth in embodiment 1 wherein the HF alkylation reactor is decommissioned.

Embodiment 3 is a method as set forth in any of the preceding embodiments, wherein the hydrogen fluoride alkylation unit further comprises a feed dryer, and the feed dryer is retained.

Embodiment 4 is a method as set forth in any of the preceding embodiments, wherein the hydrogen fluoride alkylation unit further comprises an HF acid cooler, and the HF acid cooler is decommissioned.

Embodiment 5 is a method as set forth in any of the preceding embodiments, wherein the hydrogen fluoride alkylation unit further comprises an HF storage tank under the vertical HF acid settler, and the HF storage tank under the vertical HF acid settler is decommissioned.

Embodiment 6 is a method as set forth in any of the preceding embodiments, wherein the hydrogen fluoride alkylation unit further comprises an HF regenerator, and the HF regenerator is decommissioned.

Embodiment 7 is a method as set forth in any of the preceding embodiments, wherein the hydrogen fluoride alkylation unit further comprises an HF alkylation waste treatment system comprising an HF acid neutralization pit, and said HF acid neutralization pit is retained.

Embodiment 8 is a method as set forth in any of the preceding embodiments, wherein the hydrogen fluoride alkylation unit further comprises an HF acid recontactor, and said HF acid recontactor is retained.

Embodiment 9 is a method as set forth in any of the preceding embodiments, wherein the hydrogen fluoride alkylation unit further comprises an HF alkylation propane stripper, and said HF alkylation propane stripper is decommissioned.

Embodiment 10 is a method as set forth in any of the preceding embodiments, wherein the hydrogen fluoride alkylation unit further comprises a propane KOH treater and/or a n-butane KOH treater, and said propane KOH treater and/or said n-butane KOH treater is retained.

Embodiment 11 is a method as set forth in any of the preceding embodiments, wherein the hydrogen fluoride alkylation unit further comprises at least one propane defluorinator, and said at least one propane defluorinator is retained.

Embodiment 12 is a method as set forth in any of the preceding embodiments, wherein a new sulfuric acid settler is provided.

Embodiment 13 is a method as set forth in embodiment 12 wherein the new sulfuric acid settler is vertical.

Embodiment 14 is a method as set forth in one of embodiments 1-11, wherein the hydrogen fluoride alkylation unit further comprises an HF acid settler, and the HF acid settler is retained.

Embodiment 15 is a method as set forth in embodiment 14 wherein the HF acid settler is vertical, and the vertical HF acid settler is modified to provide a vertical sulfuric acid settler.

Embodiment 16 is a method as set forth in embodiments 13 or 15, wherein the bottom section of the vertical sulfuric acid settler is segmented.

Embodiment 17 is a method as set forth in one of embodiments 12-16, wherein the sulfuric acid settler comprises at least one coalescing media.

Embodiment 18 is a method as set forth in one of embodiments 1-11, wherein the at least one sulfuric acid alkylation reactor comprises an acid settling zone inside the reactor vessel, and the converted sulfuric acid alkylation unit comprises no separate sulfuric acid settler.

Embodiment 19 is a method as set forth in any of the preceding embodiments, wherein the at least one sulfuric acid alkylation reactor is at least one internally agitated sulfuric acid alkylation reactor.

Embodiment 20 is a method as set forth in embodiment 19 wherein the internally agitated sulfuric acid alkylation reactor is a vertical sulfuric acid alkylation reactor.

Embodiment 21 is a method as set forth in embodiment 19 wherein the internally agitated sulfuric acid alkylation reactor is a horizontal sulfuric acid alkylation reactor.

Embodiment 22 is a method as set forth in one of embodiments 1-18, wherein the at least one sulfuric acid alkylation reactor is at least one externally agitated sulfuric acid alkylation reactor.

Embodiment 23 is a method as set forth in any of the preceding embodiments, wherein the hydrogen fluoride alkylation unit further comprises a remote HF storage tank, and the remote HF storage tank is retained.

Embodiment 24 is a method as set forth in any of the preceding embodiments, wherein the hydrogen fluoride alkylation unit further comprises a remote HF blowdown drum, and the remote HF blowdown drum is retained.

Embodiment 25 is a method as set forth in any of the preceding embodiments, wherein the hydrogen fluoride alkylation unit further comprises an ASO/KOH separator, and the ASO/KOH separator is retained.

Embodiment 26 is a segmented sulfuric acid settler for separating a sulfuric acid phase from a hydrocarbon phase, the sulfuric acid settler comprising: (a) a vertical vessel having an outlet at its top section, a vertical interior wall, and a bottom; (b) at least one internal vertical wall defining two or more settling chambers within the vessel; (c) an inlet for each settling chamber for ingress of a sulfuric acid/hydrocarbon emulsion; (d) an outlet for each settling chamber located below the inlet for that settling chamber for exit of the sulfuric acid phase from that settling chamber; and (e) a coalescing media extending substantially the full diameter of the vertical vessel, the coalescing media being positioned above the at least one internal vertical wall.

Embodiment 27 is a segmented sulfuric acid settler as set forth in embodiment 26 wherein the vertical vessel is substantially cylindrical.

Embodiment 28 is a segmented sulfuric acid settler as set forth in embodiments 26 or 27, wherein the at least one internal vertical wall extends upwardly from the bottom of the vertical vessel.

Embodiment 29 is a segmented sulfuric acid settler as set forth in embodiment 28 wherein the at least one internal vertical wall extends upwardly from the bottom of the vertical vessel to the coalescing media.

Embodiment 30 is a segmented sulfuric acid settler as set forth in one of embodiments 26-29, wherein the number of the internal vertical walls is three to five.

Embodiment 31 is a segmented sulfuric acid settler as set forth in embodiment 30 wherein the internal vertical walls extend substantially radially inwardly from the vertical interior wall of the vertical vessel.

Embodiment 32 is a segmented sulfuric acid settler as set forth in one of embodiments 26-31, wherein the coalescing media comprises a first coalescing media and a second coalescing media, the first coalescing media extends substantially the full diameter of the vertical vessel and is positioned above the at least one internal vertical wall, the second coalescing media extends substantially the full diameter of the vertical vessel and is spaced above the first coalescing media but below the outlet at the top section of the vessel.

Embodiment 33 is a segmented sulfuric acid settler as set forth in embodiment 32 wherein the at least one internal vertical wall extends upwardly from the bottom of the vertical vessel to the first coalescing media.

Embodiment 34 is a segmented sulfuric acid settler as set forth in embodiments 32 or 33, wherein the first coalescing media is a bulk separation coalescing media, and the second coalescing media is a fine separation coalescing media.

Embodiment 35 is a segmented sulfuric acid settler as set forth in one of embodiments 26-34, wherein the sulfuric acid settler further comprises an additional outlet for at least one settling chamber, said additional outlet is located below the inlet for that settling chamber for exit of the sulfuric acid phase from that settling chamber.

Embodiment 36 is a segmented sulfuric acid settler as set forth in one of embodiments 26-34, wherein the sulfuric acid settler further comprises an additional outlet for each settling chamber, said additional outlet is located below the inlet for that settling chamber for exit of the sulfuric acid phase from that settling chamber.

Embodiment 37 is a segmented sulfuric acid settler as set forth in embodiments 35 or 36, wherein the additional outlet is located at the bottom of the vertical vessel.

Embodiment 38 is a method for converting a hydrogen fluoride alkylation unit which utilizes hydrogen fluoride as a reaction catalyst to a sulfuric acid alkylation unit, the method comprising: (a) substituting sulfuric acid for hydrogen fluoride as the reaction catalyst; and (b) modifying a suitable vessel in the hydrogen fluoride alkylation unit to provide a segmented sulfuric acid settler as set forth in one of embodiments 26-37.

Embodiment 39 is a method as set forth in embodiment 38 wherein the hydrogen fluoride alkylation unit comprises a vertical HF acid settler, and the vertical HF acid settler is modified to provide a segmented sulfuric acid settler as set forth in one of embodiments 26-37.

Embodiment 40 is a method for converting a hydrogen fluoride alkylation unit which utilizes hydrogen fluoride as a reaction catalyst to a sulfuric acid alkylation unit, the method comprising: (a) substituting sulfuric acid for hydrogen fluoride as the reaction catalyst; and (b) providing a new segmented sulfuric acid settler as set forth in one of embodiments 26-37.

Embodiment 41 is a method as set forth in one of embodiments 38-40, further comprising: (c) providing two or more sulfuric acid alkylation reaction zones disposed in sequence, each sulfuric acid alkylation reaction zone having a sulfuric acid/hydrocarbon emulsion outlet and a sulfuric acid inlet, the number of the sulfuric acid alkylation reaction zones and the number of the settling chambers being equal; and (d) providing conduits connecting the sulfuric acid/hydrocarbon emulsion outlet and the sulfuric acid inlet of a sulfuric acid alkylation reaction zone with the inlet and the outlet of a settling chamber respectively so that each sulfuric acid alkylation reaction zone is connected or coupled with a different settling chamber to form one-to-one correspondence.

Embodiment 42 is a method as set forth in embodiment 41 further comprising: providing a conduit connecting the sulfuric acid inlet of a non-first sulfuric acid alkylation reaction zone with an outlet or an additional outlet (if present) of the immediately preceding settling chamber.

Embodiment 43 is a method as set forth in embodiment 41 further comprising: providing conduits connecting the sulfuric acid inlet of each non-first sulfuric acid alkylation reaction zone with an outlet or an additional outlet (if present) of the immediately preceding settling chamber.

Embodiment 44 is a method for converting a vertical HF acid settler to a segmented sulfuric acid settler. The vertical HF acid settler comprises a vertical vessel having an outlet at its top section, a vertical interior wall, a bottom, and an internal baffle extending upwardly from the bottom of the vertical vessel. The method comprising: (a) retaining the internal baffle to provide at least one internal vertical wall defining settling chambers within the vessel, said internal vertical wall extending upwardly from the bottom of the vertical vessel; (b) retaining the outlet which is at the top section of the vertical vessel; (c) providing a first coalescing media extending substantially the full diameter of the vertical vessel, the first coalescing media being positioned above the internal vertical wall; and (d) providing an inlet and an outlet for each of said settling chambers, the outlet of a settling chamber being positioned below the inlet of said settling chamber.

Embodiment 45 is a method as set forth in embodiment 44 further comprising: providing a second coalescing media extending substantially the full diameter of the vertical vessel, the second coalescing media being spaced above the first coalescing media but below the outlet at the top section of the vertical vessel.

Embodiment 46 is a method as set forth in embodiments 44 or 45, further comprising: (e) installing additional one or more internal vertical walls defining additional settling chambers within the vessel, said additional one or more internal vertical walls extending upwardly from the bottom of the vertical vessel and having substantially the same height as the at least one internal vertical wall converted from the internal baffle; and (f) providing an inlet and an outlet for each of said additional settling chambers, the outlet of a settling chamber being positioned below the inlet of said settling chamber.

Embodiment 47 is a method for converting a vertical HF acid settler to a segmented sulfuric acid settler. The vertical HF acid settler comprises a vertical vessel having an outlet at its top section, a vertical interior wall, a bottom, and internal components comprising an internal baffle extending upwardly from the bottom of the vertical vessel. The method comprising: (a) removing the internal components from the vertical vessel; (b) installing one or more internal vertical walls defining two or more settling chambers within the vessel, said one or more internal vertical walls extending upwardly from the bottom of the vertical vessel; (c) retaining the outlet which is at the top section of the vertical vessel; (d) providing a first coalescing media extending substantially the full diameter of the vertical vessel, the first coalescing media being positioned above the one or more internal vertical walls; and (e) providing an inlet and an outlet for each of said two or more settling chambers, the outlet of a settling chamber being positioned below the inlet of said settling chamber.

Embodiment 48 is a method as set forth in embodiment 47 further comprising: providing a second coalescing media extending substantially the full diameter of the vertical vessel, the second coalescing media being spaced above the first coalescing media but below the outlet at the top section of the vertical vessel.

Embodiment 49 is a method as set forth in one of embodiments 44-48, further comprising: providing an additional outlet at the bottom of at least one settling chamber.

Embodiment 50 is a method as set forth in one of embodiments 44-48, further comprising: providing an additional outlet at the bottom of each settling chamber.

Embodiment 51 is a converted sulfuric acid alkylation unit comprising a segmented sulfuric acid settler as set forth in one of embodiments 26-37.

Embodiment 52 is a converted sulfuric acid alkylation unit as set forth in embodiment 51 further comprising two or more sulfuric acid alkylation reaction zones disposed in sequence, wherein the number of the sulfuric acid alkylation reaction zones and the number of the settling chambers are equal.

Embodiment 53 is a converted sulfuric acid alkylation unit as set forth in embodiment 52 wherein each sulfuric acid alkylation reaction zone has a sulfuric acid/hydrocarbon emulsion outlet and a sulfuric acid inlet, the emulsion outlet and the sulfuric acid inlet of each sulfuric acid alkylation reaction zone is fluidly connected with the inlet and the outlet of a different settling chamber respectively.

Embodiment 54 is a converted sulfuric acid alkylation unit as set forth in embodiment 53 wherein the sulfuric acid inlet of a non-first sulfuric acid alkylation reaction zone is fluidly connected with an outlet or an additional outlet (if present) of the immediately preceding settling chamber.

Embodiment 55 is a converted sulfuric acid alkylation unit as set forth in embodiment 54 wherein the sulfuric acid inlet of each non-first sulfuric acid alkylation reaction zone is fluidly connected with an outlet or an additional outlet (if present) of the immediately preceding settling chamber.

Embodiment 56 is an alkylation process comprising contacting an olefin with an isoparaffin in the presence of a sulfuric acid catalyst to produce a product mixture comprising an alkylate wherein the contacting is performed in the two or more sulfuric acid alkylation reaction zones of the converted sulfuric acid alkylation unit as set forth in one of embodiments 52-55.

What is claimed is:

1. A method for converting a hydrogen fluoride alkylation unit which utilizes hydrogen fluoride as a reaction catalyst to a sulfuric acid alkylation unit, the hydrogen fluoride alkylation unit comprising an HF alkylation reactor, an HF alkylation fractionation section comprising at least one fractionator, and an HF acid relief neutralizer vessel, the method comprising:
    (a) substituting sulfuric acid for hydrogen fluoride as the reaction catalyst;
    (b) retaining the HF acid relief neutralizer vessel as a blowdown vapor scrubber;
    (c) retaining the HF alkylation fractionation section as a sulfuric acid alkylation fractionation section;
    (d) providing at least one sulfuric acid alkylation reactor;
    (e) providing a refrigeration section comprising a refrigerant compressor and a heat exchanger for condensing a vapor stream from the refrigerant compressor;
    (f) providing a conduit for recycling an isoparaffin comprising isobutane from the refrigeration section to said at least one sulfuric acid alkylation reactor; and
    (g) providing a feed/effluent heat exchanger for cooling a hydrocarbon feed stream and heating a net effluent stream.

2. A segmented sulfuric acid settler for separating a sulfuric acid phase from a hydrocarbon phase, the sulfuric acid settler comprising:
    (a) a vertical vessel having an outlet at its top section, a vertical interior wall, and a bottom;
    (b) at least one internal vertical wall defining two or more settling chambers within the vessel;
    (c) an inlet for each settling chamber for ingress of a sulfuric acid/hydrocarbon emulsion;
    (d) an outlet for each settling chamber located below the inlet for that settling chamber for exit of the sulfuric acid phase from that settling chamber; and
    (e) a coalescing media extending substantially the full diameter of the vertical vessel, the coalescing media being positioned above the at least one internal vertical wall.

3. The segmented sulfuric acid settler of claim 2, wherein the coalescing media comprises a first coalescing media and a second coalescing media, the first coalescing media extends substantially the full diameter of the vertical vessel and is positioned above the at least one internal vertical wall, the second coalescing media extends substantially the full diameter of the vertical vessel and is spaced above the first coalescing media but below the outlet at the top section of the vessel.

4. The segmented sulfuric acid settler of claim 3 wherein the at least one internal vertical wall extends upwardly from the bottom of the vertical vessel to the first coalescing media.

5. A method for converting a hydrogen fluoride alkylation unit which utilizes hydrogen fluoride as a reaction catalyst to a sulfuric acid alkylation unit, the method comprising:
    (a) substituting sulfuric acid for hydrogen fluoride as the reaction catalyst; and
    (b) modifying a suitable vessel in the hydrogen fluoride alkylation unit to provide a segmented sulfuric acid settler as set forth in claim 2.

6. The method of claim 5 wherein the hydrogen fluoride alkylation unit comprises a vertical HF acid settler, and the vertical HF acid settler is modified to provide the segmented sulfuric acid settler.

7. A method for converting a hydrogen fluoride alkylation unit which utilizes hydrogen fluoride as a reaction catalyst to a sulfuric acid alkylation unit, the method comprising:
    (a) substituting sulfuric acid for hydrogen fluoride as the reaction catalyst; and
    (b) providing a new segmented sulfuric acid settler as set forth in claim 2.

8. The method as in claim 5, further comprising:
(c) providing two or more sulfuric acid alkylation reaction zones disposed in sequence, each sulfuric acid alkylation reaction zone having a sulfuric acid/hydrocarbon emulsion outlet and a sulfuric acid inlet, the number of the sulfuric acid alkylation reaction zones and the number of the settling chambers being equal; and
(d) providing conduits connecting the sulfuric acid/hydrocarbon emulsion outlet and the sulfuric acid inlet of a sulfuric acid alkylation reaction zone with the inlet and the outlet of a settling chamber respectively so that each sulfuric acid alkylation reaction zone is connected or coupled with a different settling chamber to form one-to-one correspondence.

9. The method of claim 8 further comprising: providing a conduit connecting the sulfuric acid inlet of a non-first sulfuric acid alkylation reaction zone with an outlet or an additional outlet (if present) of the immediately preceding settling chamber.

10. A converted sulfuric acid alkylation unit comprising a segmented sulfuric acid settler as set forth in claim 2.

11. The method as in claim 7, further comprising:
(c) providing two or more sulfuric acid alkylation reaction zones disposed in sequence, each sulfuric acid alkylation reaction zone having a sulfuric acid/hydrocarbon emulsion outlet and a sulfuric acid inlet, the number of the sulfuric acid alkylation reaction zones and the number of the settling chambers being equal; and
(d) providing conduits connecting the sulfuric acid/hydrocarbon emulsion outlet and the sulfuric acid inlet of a sulfuric acid alkylation reaction zone with the inlet and the outlet of a settling chamber respectively so that each sulfuric acid alkylation reaction zone is connected or coupled with a different settling chamber to form one-to-one correspondence.

12. A method for converting a vertical HF acid settler to a segmented sulfuric acid settler, the vertical HF acid settler comprising a vertical vessel having an outlet at its top section, a vertical interior wall, a bottom, and an internal baffle extending upwardly from the bottom of the vertical vessel, the method comprising:
(a) retaining the internal baffle to provide at least one internal vertical wall defining settling chambers within the vessel, said internal vertical wall extending upwardly from the bottom of the vertical vessel;
(b) retaining the outlet which is at the top section of the vertical vessel;
(c) providing a first coalescing media extending substantially the full diameter of the vertical vessel, the first coalescing media being positioned above the internal vertical wall; and
(d) providing an inlet and an outlet for each of said settling chambers, the outlet of a settling chamber being positioned below the inlet of said settling chamber.

13. The method of claim 12 further comprising: providing a second coalescing media extending substantially the full diameter of the vertical vessel, the second coalescing media being spaced above the first coalescing media but below the outlet at the top section of the vertical vessel.

14. The method of claim 12, further comprising:
(e) installing additional one or more internal vertical walls defining additional settling chambers within the vessel, said additional one or more internal vertical walls extending upwardly from the bottom of the vertical vessel and having substantially the same height as the at least one internal vertical wall converted from the internal baffle; and
(f) providing an inlet and an outlet for each of said additional settling chambers, the outlet of a settling chamber being positioned below the inlet of said settling chamber.

15. A method for converting a vertical HF acid settler to a segmented sulfuric acid settler, the vertical HF acid settler comprising a vertical vessel having an outlet at its top section, a vertical interior wall, a bottom, and internal components comprising an internal baffle extending upwardly from the bottom of the vertical vessel, the method comprising:
(a) removing the internal components from the vertical vessel;
(b) installing one or more internal vertical walls defining two or more settling chambers within the vessel, said one or more internal vertical walls extending upwardly from the bottom of the vertical vessel;
(c) retaining the outlet which is at the top section of the vertical vessel;
(d) providing a first coalescing media extending substantially the full diameter of the vertical vessel, the first coalescing media being positioned above the one or more internal vertical walls; and
(e) providing an inlet and an outlet for each of said two or more settling chambers, the outlet of a settling chamber being positioned below the inlet of said settling chamber.

16. The method of claim 15 further comprising: providing a second coalescing media extending substantially the full diameter of the vertical vessel, the second coalescing media being spaced above the first coalescing media but below the outlet at the top section of the vertical vessel.

* * * * *